US007001724B1

(12) United States Patent
Greenfield

(10) Patent No.: US 7,001,724 B1
(45) Date of Patent: Feb. 21, 2006

(54) COMPOSITIONS, METHODS, AND KITS FOR ISOLATING NUCLEIC ACIDS USING SURFACTANTS AND PROTEASES

(75) Inventor: I. Lawrence Greenfield, San Mateo, CA (US)

(73) Assignee: Applera Corporation, Foster City, CA (US)

( * ) Notice: Subject to any disclaimer, the term of this patent is extended or adjusted under 35 U.S.C. 154(b) by 85 days.

(21) Appl. No.: 09/724,613

(22) Filed: Nov. 28, 2000

(51) Int. Cl.
*C12Q 1/68* (2006.01)
*C12N 1/00* (2006.01)
*C07H 19/00* (2006.01)
*C07H 21/02* (2006.01)
*C07H 23/00* (2006.01)

(52) U.S. Cl. .................. 435/6; 435/243; 536/23.1; 536/26.42; 536/27.12

(58) Field of Classification Search .................. 435/6, 435/243; 536/23.1, 26.42, 27.12
See application file for complete search history.

(56) References Cited

U.S. PATENT DOCUMENTS

| 4,481,294 | A | | 11/1984 | Downs |
| 4,900,677 | A | * | 2/1990 | Hewitt ........................ 435/259 |
| 4,943,530 | A | * | 7/1990 | Christner et al. ........... 435/188 |
| 5,010,183 | A | | 4/1991 | Macfarlane |
| 5,130,423 | A | * | 7/1992 | Ness et al. ................ 536/25.42 |
| 5,300,635 | A | | 4/1994 | Macfarlane |
| 5,596,092 | A | | 1/1997 | Schneider |
| 5,728,822 | A | | 3/1998 | Macfarlane |
| 6,242,188 | B1 | * | 6/2001 | Dattagupta et al. ............ 435/6 |
| 6,548,256 | B1 | | 4/2003 | Lienau et al. .................. 435/6 |
| 6,762,027 | B1 | | 7/2004 | Greenfield et al. |
| 2005/0009045 | A1 | | 1/2005 | Greenfield et al. |

FOREIGN PATENT DOCUMENTS

| DE | 199 37 607 A1 | 2/2001 |
| EP | 1 018 549 A1 | 7/2000 |
| WO | WO 95/15970 | 6/1995 |
| WO | WO 98/04730 | 2/1998 |
| WO | WO 98/20164 | 5/1998 |

OTHER PUBLICATIONS

International Search Report for PCT Application No. PCT/US01/45071, mailed Dec. 27, 2002.
Chapdelaine, P. et al., "A One-Hour Procedure for the Preparation of Genomic DNA from Frozen Tissues," *Bio Techniques*, 14(2):163-164, 1993.
Colosi, J. C. et al., "Tissue Grinding with Ball Bearings and Vortex Mixer for DNA Extraction," *Nucleic Acid Research*, 21(4):1051-1052, 1993.
Dry, P.J., "A Quick and Easy Method for the Purification of DNA From Chorionic Villus Samples," *Nucleic Acids Research*, 16(15):7730, 1988.
Fisher, J. A., "Activity of Proteinase K and RNase in Guanidinium Thiocyanate," *Techniques in Molecular Biology and Cloning*, Abstract 4823, FASEB Journal, 1988.

(Continued)

*Primary Examiner*—Jezia Riley
(74) *Attorney, Agent, or Firm*—Scott Bortner; Finnegan, Henderson, Farabow, Garrett & Dunner, L.L.P.

(57) ABSTRACT

The invention provides compositions and methods for releasing and for isolating nucleic acids from biological samples, preferably from whole tissue, using cationic surfactants and proteases. The surfactant-protease combinations, when used with whole tissue, macerate the tissue, lyse individual cells, release nucleic acids, and inactivate nucleases. Kits for isolating nucleic acids from biological samples, particularly from whole tissue, are also provided.

47 Claims, 14 Drawing Sheets

OTHER PUBLICATIONS

Goldenberger, D. et al., "A Simple 'Universal' DNA Extraction Procedure Using SDS and Proteinase K is Compatible with Direct PCR Amplification," *PCR Methods and Applications*, 4:368-370, 1995.

Lai, C.-C. et al., "Improved Proteinase K Digestion for the Rapid Isolation of mRNA from Mammalian Tissues," *BioTechniques*, 15(4):620-624, 1993.

Laird, P. W. et al., "Simplified Mammalian DNA Isolation Procedure," *Nucleic Acids Research*, 19(15):4293, 1991.

Macfarlane, D. E. et al., "Isolating RNA from Clinical Samples With Catrimox-14 and Lithium Chloride," *Journal of Clinical Laboratory Analysis*, 11:132-139, 1997.

Macfarlane, D. E. et al., "Isolating RNA from Whole Blood—The Dawn of RNA-Based Diagnosis," *Nature*, 362:186-188, 1993.

Wilson, K., "Preparation of Genomic DNA from Bacteria" in *Current Protocols in Molecular Biology*, vol. 1, F.M. Ausbel et al. (Eds.), John Wiley & Sons, Inc., NY, pp. 2.4.1-2.4.5, 1994.

Richards, E., "Preparation of Genomic DNA from Plant Tissue" in *Current Protocols in Molecular Biology*, vol. 1, F.M. Ausbel et al. (Eds.), John Wiley & Sons, Inc., NY, pp. 2.3.3-2.3.7, 1994.

Rauber, N. R. K. et al., "Ribonuclease A Digestion by Proteinase K," *Z. Naturforsch.*, 33 c:660-663, 1978.

Seibert, G. et al., "The Separation of High and Low Molecular Weight RNA by Precipitation with N-Cetyl-N,N,N-trimethylammoniumbromide," *Z. Naturforsch Sect. C. Biosci.*, 32(3-4):294-296, 1977.

Wiegers, U. et al., "A New Method Using 'Proteinase K' to Prevent mRNA Degradation During Isolation from HeLa Cells," *Biochemical and Biophysical Research Communications*, 44(2):513-519, (1971).

* cited by examiner

COMPOSITIONS, METHODS, AND KITS FOR ISOLATING NUCLEIC ACIDS USING SURFACTANTS AND PROTEASES

FIELD OF THE INVENTION

The invention relates to compositions and methods for releasing and for isolating nucleic acids from biological samples, preferably from whole tissue. The invention also provides kits for isolating and/or releasing nucleic acids from biological samples.

BACKGROUND OF THE INVENTION

Current methods for isolating nucleic acids from cultured cells generally include lysing the cells and inactivating nucleases using chaotropic salts, such as guanidine hydrochloride or guanidinium thiocyanate, and a nonionic surfactant. The released nucleic acids are then selectively precipitated from solution. The combination of chaotropic salts and nonionic surfactants, however, typically are ineffective at penetrating whole tissues to release nucleic acid.

When cells are lysed to release nucleic acids, endogenous nucleases, enzymes that degrade nucleic acids (DNA and RNA), are also released. Thus, when minimally degraded (i.e., high integrity) nucleic acid is desired, one tries to minimize nuclease activity as much as possible. Deoxyribonucleases (DNAses), which are nucleases that degrade DNA, can often be inactivated by adding divalent cation chelators to the reaction compositions. Free magnesium ions, which are typically needed for DNAse activity, are bound or complexed by the addition of chelators. Thus, chelators typically diminish or inactivate endogenous DNAses. Many endogenous ribonucleases (RNAses), nucleases that degrade RNA, however, do not typically need divalent cations, such as magnesium, for their activity. Such RNAses are unaffected by the addition of chelators. To inactivate RNAses during RNA isolation procedures, therefore, one may add to the reaction composition inhibitors of RNAse activity.

Various chemical disruption methods, using surfactants, chaotropes, proteases, bile salts, organic solvents, and harsh acidic or basic conditions have been employed to lyse cells and release nucleic acid. Proteinase K, a broad specificity protease, has also been employed. To increase the activity of Proteinase K, denaturing agents, such as anionic detergents and chaotropes have been used in combination with Proteinase K. The nucleic acid obtained using such methods may be degraded due to long incubation times or exposure to harsh conditions.

Physical disruption methods using tissue homogenizers, mortar and pestle, dounce homogenization, frozen pulverization, and bead beaters, have been employed with biological samples. The nucleic acid obtained using these methods, however, is typically degraded due to shearing, long incubation times and high temperatures that may be generated using these methods. Further, such methods present health and safety concerns as a portion of the sample may be aerosolized during the physical disruption procedure. This becomes a critical issue when the sample potentially contains infectious agents such as HIV, hepatitis, or other pathogenic microorganisms.

Thus, there is a need for methods and compositions for isolating high integrity, i.e., high molecular weight, nucleic acid molecules from biological samples in a safe, rapid, and efficient manner, especially from whole tissues.

SUMMARY OF THE INVENTION

The present invention provides novel compositions, methods, and kits for releasing or for isolating nucleic acids from biological samples using at least one surfactant and at least one protease. In one aspect, compositions are provided for releasing nucleic acids from a biological sample. In certain embodiments, these compositions include at least one cationic surfactant, at least one protease, and a buffer.

In another aspect, methods for releasing and methods for isolating nucleic acids from a biological sample are provided. In certain embodiments, these methods include combining the sample with at least one cationic surfactant, at least one protease, and a buffer to form a reaction composition. Optionally, the reaction composition further comprises a second surfactant and a salt. The composition is incubated under appropriate conditions to allow the sample to be digested, releasing the nucleic acid. In certain embodiments, the released nucleic acid is then isolated. Kits for isolating and/or releasing nucleic acid from biological samples are also provided. In certain embodiments, the invention provides kits comprising at least one cationic surfactant and at least one protease. Kits further comprising a second surfactant, a salt, organic extraction agent(s), organic precipitating agent(s), solubilizing agents(s), or combinations of these components are also provided.

BRIEF DESCRIPTION OF THE FIGURES

FIG. 2: illustrates the effect of various surfactants on Proteinase K digestion of a dye-labeled casein substrate.

DETAILED DESCRIPTION OF THE INVENTION

Figure 1:
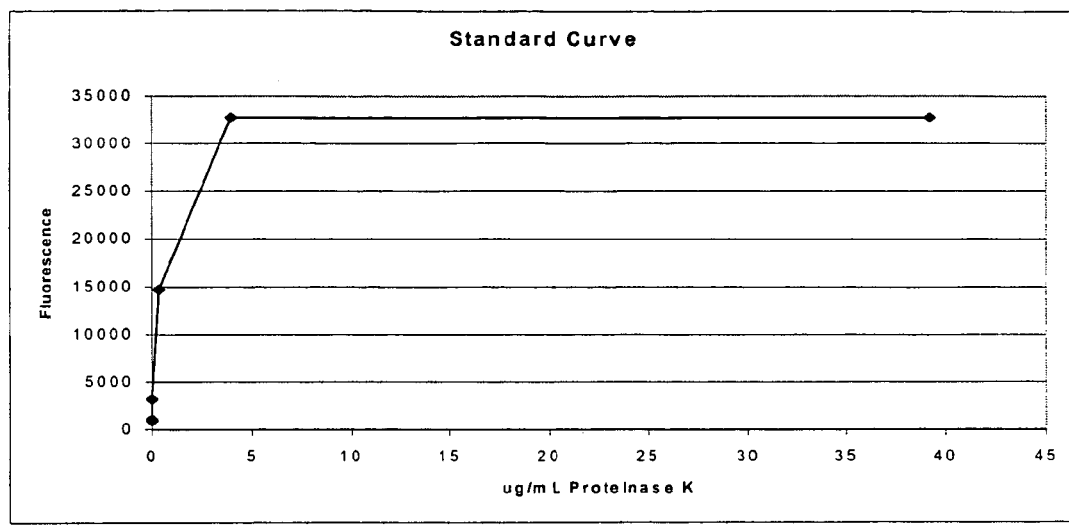
FIG. 1: represents the fluorescent intensity (measured in fluorescence units) of dye-labeled casein substrate incubated with Proteinase K at concentrations ranging from 40 fg/mL to 40 ug/mL.

The section headings used herein are for organizational purposes only and are not to be construed as limiting the subject matter described. All documents cited in this application, including, but not limited to patents, patent applications, articles, books, and treatises, are expressly incorporated by reference in their entirety for any purpose.

Definitions

The term "alkyl group" refers to a hydrocarbon moiety based on a linear, branched or cyclic alkane. Linear alkanes are organic compounds with the general chemical formula $C_nH_{2n+2}$, where C represents a carbon atom, H represents a hydrogen atom, and n represents a whole number. Exemplary linear alkanes include, but are not limited to, methane ($CH_4$), propane ($C_3H_8$), butane ($C_4H_{10}$), octane and the like. Exemplary branched alkanes include, but are not limited to, isobutane ($C_4H_{10}$), isopentane ($C_5H_{12}$), and the like. Exemplary cyclic alkanes include, but are not limited to, cyclobutane ($C_4H_8$), cyclohexane ($C_6H_{12}$), and the like. Exemplary alkyl groups include, but are not limited to, methyl (—$CH_3$), propyl (—$C_3H_7$), octyl (—$C_8H_{17}$), and the like. While alkanes are typically unreactive, alkyl groups can be combined with other molecules to form compounds. For example, isopropyl alcohol ($C_3H_7OH$) is an alcohol that contains a propyl group. A general discussion of alkyl groups and alkanes can be found, among other places, in Morrison and Boyd, Organic Chemistry, $3^{rd}$ Ed., Allyn and Bacon, Boston, Mass., 1973; and Vollhardt, Organic Chemistry, W.H. Freeman, New York, N.Y., 1987.

The term "aryl group" refers to a hydrocarbon moiety that is based on benzene or other aromatic compounds. Aryl groups, like alkyl groups, can be combined with other molecules to form compounds. A general discussion of aromatic compounds and aryl groups can be found, among other places, in Morrison and Boyd, Organic Chemistry, $3^{rd}$ Ed., Allyn and Bacon, Boston, Mass., 1973; and Vollhardt, Organic Chemistry, W.H. Freeman, New York, N.Y., 1987, particularly Chapter 19.

The term "biological sample" is used in a broad sense and is intended to include a variety of biological sources that contain nucleic acids. Such sources include, without limitation, whole tissues, including biopsy materials and aspirates; in vitro cultured cells, including primary and secondary cells, transformed cell lines, and tissue and cellular explants; whole blood, red blood cells, white blood cells, and lymph; body fluids such as urine, sputum, semen, secretions, eye washes and aspirates, lung washes and aspirates; and the like. Microorganisms and viruses that may be present on or in a biological sample are within the scope of the invention.

The term "buffer," as used herein, refers to aqueous solutions or compositions that resist changes in pH when acids or bases are added to the solution. This resistance to pH change is due to the solution's buffering action. Solutions exhibiting buffering activity are referred to as buffers or buffer solutions. Buffers typically do not have an unlimited ability to maintain the pH of a solution or composition. Rather, typically they are able to maintain the pH within certain ranges, for example between pH 5 and pH 7. See, generally, C. Mohan, Buffers, A guide for the preparation and use of buffers in biological systems, Calbiochem, 1999. Exemplary buffers include, but are not limited to, MES ([2-(N-Morphilino)ethanesulfonic acid]), ADA (N-2-Acetamido-2-iminodiacetic acid), and Tris ([tris(Hydroxymethyl)aminomethane]; also known as Trizma); Bis-Tris; ACES; PIPES; MOPS; and the like (all available from Sigma).

Buffers that maintain the pH within a certain pH range, for example, between pH 5 and pH 7, and similar terms as used herein, are intended to encompass any buffer that exhibits buffering action at some point within the stated pH range. Thus, that term encompasses buffers that do not exhibit buffering capacity within the entire stated range, and buffers with buffering capacity that extend beyond the stated range. For example, solution A may exhibit buffering capacity between pH 5.2 and 6.7, solution B may exhibit buffering capacity between 6.0 and 8.0. For purposes of this invention, both of those solutions would be considered buffers that maintain the pH within the range of pH 5.0 to pH 7.0. The skilled artisan will be able to identify an appropriate buffer for maintaining the pH between a specified range using a buffer table. Buffer tables can be found in, among other places, the Calbiochem 2000–2001 General Catalog at pages 81–82, and the Sigma 2000–2001 Biochemicals and Reagents for Life Science Research Catalog at page 1873, both of which are expressly incorporated by reference.

The term "chaotrope" or "chaotropic salt," as used herein, refers to a substance that causes disorder in a protein or nucleic acid by, for example, but not limited to, altering the secondary, tertiary, or quaternary structure of a protein or a nucleic acid while leaving the primary structure intact. Exemplary chaotropes include, but are not limited to, guanidine hydrochloride, guanidinium thiocyanate, sodium thiocyanate, sodium iodide, sodium perchlorate, urea, and the like. A typical anionic chaotropic series, shown in order of decreasing chaotropic strength, includes: $CCl_3COO^- >> CNS^- > CF_3COO^- > ClO_4^- > I^- > CH_3COO^- \rightarrow Br^-$, Cl⁻, or $CHO_2^-$. Descriptions of chaotropes and chaotropic salts can be found, among other places, in Hamaguchi, Kozo and Geiduschek; E. Peter; Hatefi, Y. and Hanstein, W. G. (1962), "Solubilization of Particulate Proteins And Nonelectrolytes by Chaotropic Agents," Proc. Natl. Acad. Sci. 62: 1129–1136); The Effect Of Electrolytes On The Stability Of The Deoxyribonucleate Helix, J. Amer. Chem. Soc. 84:1329–1338); and U.S. Pat. No. 5,234,809.

A "chelator" is a cyclic or heterocyclic ring compound that is capable of binding to metal cations, such as sodium ($Na^+$), magnesium ($Mg^{++}$), or calcium ($Ca^{++}$) ions. At least two non-metal ions of the chelator form coordinate bonds with the metal cation to incorporate it into the ring. Thus, the metal cation is no longer free to participate in other reactions. Cations that have a single charge, such as $Na^+$ are referred to as monovalent cations, while those with a double charge, such as $Mg^{++}$ or $Ca^{++}$, are referred to as divalent cations. Some enzymes, such as certain polymerases and nucleases typically function in the presence of free divalent cations. Thus, a divalent cation chelator, provided in sufficient amounts, typically would inhibit or reduce the activity of such divalent cation-dependent enzymes. Exemplary chelators include, but are not limited to, EDTA, EGTA, diaminoethane, and the like.

A "nuclease," such as a deoxyribonuclease (DNAse) or a ribonuclease (RNAse), is an enzyme that catalyzes the hydrolysis of phosphodiester linkages in nucleic acid polymers. Nucleases cause nucleic acid polymers to degrade, releasing constituent nucleotides and/or oligonucleotides (fragments of the polymers). A DNAse degrades DNA molecules and an RNAse degrades RNA molecules. Nuclease activity can typically be slowed or prevented by appropriate nuclease inhibitors.

As used herein, the term "organic solvent" refers to organic liquids, i.e., those comprising molecules with a hydrocarbon backbone. Organic solvents are capable of solvating non-solvent molecules, e.g., by surrounding them with solvent molecules so that the non-solvent molecules are dissolved in the solvent. Exemplary organic solvents include, but are not limited to, benzene, carbon tetrachloride, chloroform, phenol and other alcohols such as ethanol, methanol, and isopropanol (2-propanol), dimethyl sulfoxide (DMSO), and the like. Organic solvents can be used, for example, to extract nucleic acids from certain biochemical compositions, or to precipitate nucleic acids from aqueous solutions. Discussions of organic solvents can be found, among other places, in Morrison & Boyd, Organic Chemistry, 3d Edition, Allyn & Bacon, Boston, Mass., 1973.

As used herein, the term "protease" refers to an enzyme that catalyzes the cleavage of peptide bonds, e.g., in proteins, polypeptides, oligopeptides, and peptides (collectively "peptides"). Exemplary proteases include, but are not limited to, subtilisins, subtilases, alkaline serine proteases, and the like. Subtilases are a family of serine proteases, i.e., enzymes that cleave peptides after the amino acid serine. Subtilases are found in prokaryotic and eukaryotic organisms, such as bacteria, fungi, yeast, and higher organisms. Subtilisins are bacterial serine proteases that have broad substrate specificities. Subtilisins are relatively resistant to denaturation by chaotropes, such as urea and guanidine hydrochloride, and anionic detergents, such as sodium dodecyl sulfate. Exemplary subtilisins include, but are not limited to: Proteinase K; Proteinase R; Proteinase T (isolated from *Tritirachium album* Limber); Subtilisin DY, Carlsberg, also referred to as Subtilisin, Subtilisin A, Subtilopeptidase A, or Alcalase Novo; BPN', also referred to as Nagarse proteinase, Nagarse, or Subtilopeptidase C; Novo, also referred to as Bacterial proteinase Novo, Subtilisin B, or Subtilopeptidase B; mesentericopeptidase; Thermitase; and the like. Discussions of subtilases, subtilisins, Proteinase K, and other proteases may be found, among other places, in Genov et al., (1995) Stability Of Subtilisins And Related Proteinases (Subtilases), Int. J. Peptide Protein Res. 45: 391–400); Narhi and Arakawa (1989) Sodium Dodecyl Sulfate Polyacrylamide Gel Electrophoresis As A Method For Studying The Stability Of Subtilisin, Biochimica et Biophysica Acta. Vol. 990: 144–149); Dixon and Webb, Enzymes, 3d Edition, Academic Press, New York, N.Y. (1979); and Creighton, Proteins: Structures and Molecular Principles, W.H. Freeman and Co., New York, N.Y. (1984).

The term "salt" as used herein, refers to a compound produced by the interaction of an acid and a base. Exemplary salts include, but are not limited to, sodium chloride (table salt), potassium phosphate, sodium bicarbonate, and the like. In water and other aqueous solutions, salts typically dissociate into an "anion" or negatively charged subcomponent, and a "cation" or positively charge subcomponent. For example, when sodium chloride (NaCl) is dissolved in water, it dissociates into a sodium cation ($Na^+$) and a chloride anion (Cl⁻).

As used herein, the term "surfactant" refers to a surface-active agent that generally comprises a hydrophobic portion and a hydrophilic portion. Examples of surfactants include, but are not limited to, detergents and bile acid salts. (See, e.g., Bhairi, A Guide to the Properties and Uses of Detergents in Biological Systems, Calbiochem-Novabiochem Corp. 1997). Surfactants may be categorized as anionic, nonionic, zwitterionic, or cationic, depending on whether they comprise one or more charged group. Anionic surfactants, such as SDS or lauryl sarkosine, contain a negatively charged group and have a net negative charge. Nonionic surfactants contain non-charged polar groups and have no charge. Exemplary nonionic surfactants include, but are not limited to, Tween 20, Triton X-100, NP-40, and the like. A zwitterionic surfactant contains both a positively charged group and a negatively charged group, and thus they are also uncharged.

A "cationic surfactant" has a positively charged group under the conditions examined. Cationic surfactants may contain quaternary amines or tertiary amines. Exemplary quaternary amine surfactants include, but are not limited to, cetylpyridinium chloride, cetyl trimethyl ammonium bromide (CTAB; Calbiochem #B22633 or Aldrich #85582-0), cetyl trimethyl ammonium chloride (CTACI; Aldrich #29273-7), dodecyl trimethyl ammonium bromide (Sigma #D-8638), octyl trimethyl ammonium bromide, tetradecyl trimethyl ammonium bromide, octadecylyl trimethyl ammonium bromide, stearoalkonium chloride, olealkonium chloride, cetrimonium chloride, alkyl trimethyl ammonium methosulfate, palmitamidopropyl trimethyl chloride, quaternium 84 (Mackernium NLE; Mcintyre Group, Ltd.), wheat lipid epoxide (Mackernium WLE; Mcintyre Group, Ltd.), and the like. Exemplary ternary amine surfactants include, but are not limited to, octyidimethylamine, decyldimethylamine, dodecyidimethylamine, tetradecyldimethylamine, hexadecyidimethylamine, octyidecyldimethylamine, octyldecylmethylamine, didecylmethylamine, dodecylmethylamine, triacetylammonium chloride, cetrimonium chloride, alkyl dimethyl benzyl ammonium chloride, and the like.

The term "whole tissue" according to the present invention is used in the broad sense to include any collection of cells organized to perform a specific function. Examples of tissues include, without limitation: muscles, including cardiac, striated, and smooth muscle; organs, such as kidney, liver, spleen, brain, etc.; nerves; dermal and epidermal layers, such as skin; connective tissue such as bone, cartilage, ligaments, and tendons; and the like. Fragments, pieces, sections, slices, and sub-components of whole tissues are within the scope of the invention. The term whole tissue is not limited, for example, to an entire organ or bone. Any aggregate or assembly of cells at any level is, for purposes of this invention, considered whole tissue. Plant tissues, such as leaves, roots, stems, and the like, are also within the scope of the present invention.

The term "nucleic acid," as used herein, refers to a polymer of ribonucleosides or deoxyribonucleosides comprising phosphodiester linkages between subunits. Such nucleic acids include, but are not limited to, genomic DNA, hnRNA, mRNA, rRNA, tRNA, fragmented nucleic acid, nucleic acid obtained from subcellular organelles such as mitochondria or chloroplasts, and nucleic acid obtained from microorganisms or DNA or RNA viruses that may be present on or in a biological sample.

Solid phase components that are capable of binding to nucleic acids released from a biological sample include a variety of materials that are capable of binding nucleic acids under suitable conditions. Exemplary solid phase components include, but are not limited to, silica particles, silicon dioxide, diatomaceous earth, glass, alkylsilica, aluminum silicate, borosilicate, nitrocellulose, diazotized paper, hydroxyapatite, nylon, metal oxides, zirconia, alumina, diethylaminoethyl- and triethylaminoethyl-derivatized supports (Chromegabond SAX, LiChrosorb-AN, Nucleosil SB, Partisil SAX, RSL Anion, Vydac TP Anion, Zorbax SAX, Nucleosil $NMe_2$, Aminex A-series, Chromex, and Hamilton HA Ionex SB, DEAE sepharose, QAE sepharose), hydrophobic chromatography resins (such phenyl- or octyl-sepharose), and the like.

Certain polymers, under appropriate conditions, are capable of precipitating nucleic acids from solution. Some polymers are capable of forming a nucleic acidpolymer complex that has a low solubility or is insoluble, so that complexed nucleic acid may precipitate. Examples of polymers that form such complexes with nucleic acids include, but are not limited to, polyethyleneimine, DEAE dextran, polylysine, polyarginine, polyhistidine, other weakly basic polymers (described in, among other places, U.S. Pat. Nos. 5,582,988; 5,733,762; 5,622,822; and 5,599,667), and the like. Other polymers, such as polyethylene glycol, bind significant amounts of water in a solution, which may also cause nucleic acids to precipitate from the solution.

Exemplary Embodiments of the Invention

The present invention is directed to compositions, methods, and kits for isolating nucleic acid from biological samples, preferably whole tissue. The compositions, methods, and kits of the invention reduce the time needed for sample preparation, decrease potential safety risks posed by multi-step procedures that require repeated sample manipulation, and provide high integrity (i.e., minimally degraded) high molecular weight nucleic acid.

The compositions and kits comprise and the methods employ surfactants and proteases. The biological sample is combined with at least one cationic surfactant and at least one protease to form a reaction composition. The reaction composition is then incubated in a manner such that nucleic acids are released from the biological samples. For example, during incubation, these reaction compositions typically can: (i) macerate or disaggregate the biological sample; (ii) lyse the cells comprising the sample; (iii) sterilize the sample; (iv) neutralize or inactivate nucleases; and (v) release nucleic acids from the biological sample.

While Proteinase K alone will effectively macerate whole tissue when incubated for approximately 12–18 hours, the released nucleic acid is frequently highly degraded. This degradation is due, at least in part, to nucleases present within the sample. The maceration process can be accelerated, as disclosed herein, by the addition of a cationic surfactant to the reaction composition. Under appropriate conditions, in certain embodiments, high integrity nucleic acid can be efficiently obtained from biological samples in 60 minutes or less using the compositions and methods of the invention. Thus, the compositions and methods of the invention provide an unexpected advantage.

Some cationic surfactants, under appropriate conditions, form a complex with the released nucleic acid and precipitate. These cationic surfactant:nucleic acid complexes may be dissolved using a nonionic surfactant and an appropriate salt. Thus, in certain embodiments, the compositions further comprise a second surfactant and a salt.

In certain embodiments, the released nucleic acid is isolated. Nucleic acids can be isolated effectively from aqueous solutions that contain biomolecules, such as lipids, proteins, and the like, using organic solvents. For example, organic solvents such as phenol or combinations of phenol and chloroform can be used to extract the nucleic acids from such solutions. The extracted nucleic acids can be isolated by precipitating the nucleic acid using, for example, alcohols such as ethanol, propanol, or butanol. In other embodiments, the released nucleic acid is not isolated from the reaction composition.

Nucleic acids may also be isolated from the reaction composition using certain polymers or divalent cations for precipitating the nucleic acids. Exemplary polymers for precipitating nucleic acids include, but are not limited to, polyethylene glycol, polyethyleneimine, DEAE dextran, polylysine, polyarginine, polyhistidine, and other weakly basic polymers. Descriptions of such polymers may be found, among other places, in U.S. Pat. Nos. 5,582,988; 5,733,762; 5,622,822; and 5,599,667. Certain divalent cations may also cause nucleic acid molecules to selectively precipitate from solution. Examples of such divalent cations include, but are not limited to, zinc chloride, magnesium chloride and magnesium sulfate.

Additionally, nucleic acids may be isolated using solid phase supports that selectively bind nucleic acids. For example, but not limited to, nucleic acids from a sample can be adsorbed to a solid phase in the presence of high concentrations of a chaotrope or salt. The solid phase may be washed to remove contaminating material, and the nucleic acid can be eluted from the solid phase using a solution with a low ionic strength. Suitable solid phases include, but are not limited to, silica particles, silicon dioxide, diatomaceous earth, glass, alkylsilica, aluminum silicate, or borosilicate.

Also, nucleic acids can be bound to an ion exchange resin in the presence of low ionic strength. Following removal of the contaminating components by washing, the nucleic acid is eluted from the solid phase by increasing the ionic strength. Exemplary ion-exchange resins include, but are not limited to, diethylaminoethyl- and triethylaminoethyl-derivatized supports (Chromegabond SAX, LiChrosorb-AN, Nucleosil SB, Partisil SAX, RSL Anion, Vydac TP Anion, Zorbax SAX, Nucleosil $NMe_2$, Aminex Aseries, Chromex, and Hamilton HA Ionex SB, DEAE sepharose, or QAE sepharose, and the like). The skilled artisan will appreciate that other solid phase materials may also be used, for example, but not limited to, nitrocellulose, diazotized paper, hydroxyapatite, nylon, metal oxides, zirconia, alumina, and reverse-phase resins (such octyl or phenyl sepharose).

The compositions of the invention include at least one protease. In certain embodiments, proteases such as subtilisins, subtilases, and alkaline serine proteases are employed. Exemplary proteases include, but are not limited to, Proteinase R, Proteinase T, subtilisin DY, dispase, subtilisin Carlsberg, subtilopeptidase A, thermolysin, thermostable proteases (such as those from Thermus Rt41A and *Bacillus thermoproteolyticus* rokko), and alkaline serine proteases form *Streptomyces griseus* or *Bacillus licheniformis*. A preferred protease, according to certain embodiments, is Proteinase K.

Certain proteases, including Proteinase K, are typically stabilized by the presence of calcium chloride. When calcium chloride is combined with certain anionic surfactants, such as SDS, a relatively insoluble precipitate can be formed. To avoid such precipitation, scientists sometimes omit calcium chloride when employing both protease and anionic surfactants. In preferred embodiments of the invention in which no substantial amount of anionic surfactants are employed, calcium chloride may be included.

To obtain high integrity DNA, in certain embodiments, DNAse inhibitors may be added to the compositions of the invention. For example, many endogenous DNAses are inhibited by divalent cation chelators, such as EDTA (ethylenediaminetetraacetic acid), EGTA ([ethyleneglycol-bis(-aminoethyl)-N,N,N',N'-tetraacetic acid]), DTPA (diethylenetriaminepentaacetic acid), and the like.

In certain embodiments, the at least one cationic surfactant comprises a quaternary amine, a tertiary amine, or both. In certain embodiments, the at least one cationic surfactant comprises cetyltrimethylammonium bromide (CTAB), cetyltrimethylammonium chloride (CTACl), hexadecyltrimethylammonium bromide (HDTAB), or hexadecyltrimethylammonium chloride (HDTACl), and the at least one protease comprises Proteinase K.

In certain embodiments, isolating the nucleic acid comprises extracting the nucleic acid with an organic agent, such as, but without limitation, phenol, chloroform, or both phenol and chloroform. In certain embodiments, the nucleic acid may be precipitated with an organic agent, for example, without limitation, an alcohol such as isopropanol, ethanol, or butanol. A combination of extracting the nucleic acid with an organic agent and precipitating the extracted nucleic acid with an organic agent is also within the scope of isolating the nucleic acid.

In certain embodiments, methods for isolating ribonucleic acid from a biological sample are provided comprising using a cationic surfactant, a protease, and a buffer. In certain embodiments, the cationic surfactant is CTAB (Sigma or Aldrich), CTACl (Sigma or Aldrich), HDTAB (Sigma #H-5882 or Fluka #52367), or HDTACl (Fluka #41199). When high integrity RNA is desired, the presence of endogenous RNAses sometimes limit the efficiency of some current procedures. Two components of the instant compositions and methods, however, can counteract the activity of endogenous RNAses, enhancing the isolation of high integrity RNA. First, Proteinase K has been shown to inactivate RNAse. Second, cationic surfactants may form complexes with RNA, decreasing the susceptibility of the RNA to RNAse degradation. See, e.g., Dahl, C. E. and Macfarlane, D. E., Isolation Of RNA From Cells In Culture Using Catrimox-14™ Cationic Surfactant, BioTechniques Vol. 15, No. 6: 1102–1105 (1993); Macfarlane, D. E. and Dahle, C. E., Isolation RNA From Whole Blood—The Dawn Of RNA-Based Diagnosis? Nature, Vol. 362: 186–188 (1993); Macfarlane, D. E. and Dahle, C. E., Isolating RNA From Clinical Samples With Catrimox-14 and Lithium Chloride, Journal of Clinical Laboratory Analysis. 11: 132–139 (1997).

According to certain embodiments, endogenous RNAse activity is further diminished using the compositions and methods of the invention. For example, RNAses are less active at lower pH, e.g., between pH 5 and 7, and temperatures below 50° C. Acridine orange can also decreases the nucleolytic activity of RNAse, presumably by interacting with the released RNA molecules making them less susceptible to degradation. RNAse inhibitors may also be added to limit or prevent RNAse activity.

Exemplary RNAse inhibitors include, but are not limited to, aurintricarboxylic acid, vanadylate ribonucleoside complexes, phenylglyoxal, p-hydroxyphenylglyoxal, polyamines, spermidine, 9-aminoacridine, iodoacetate, bentonite, poly[2'-O-(2,4-dinitrophenyl)]poly(adenyhlic acid), zinc sulfate, bromopyruvic acid, formamide, dimethylformamide, copper, zinc, and the like. In certain embodiments, the compositions and methods of the invention comprise at least one RNAse inhibitor.

According to certain embodiments, cationic surfactants used in the compositions and methods have the general chemical formula:

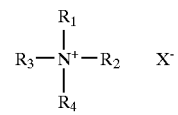

($N^+R_1R_2R_3R_4$:$X^-$), where the cation moieties $R_1$, $R_2$, $R_3$, and $R_4$ independently may be:—H, an alkyl group containing up to 20 carbon atoms, or an aryl group containing between 6 and 26 carbon atoms; wherein at least one of $R_1$, $R_2$, $R_3$, or $R_4$ contains an alkyl group of at least 6 carbons; and where $X^-$ is an anion. For example, the cationic surfactant may be an alkyltrimethyl ammonium salt, where $R_1$, $R_2$, and $R_3$ are methyl groups, and $R_4$ is an alkyl group comprising 6, 8, 10, 12, 14, 16, or 18 carbon atoms. The cationic subcomponent ($N^+R_1R_2R_3R_4$) of the alkyltrimethyl ammonium salt might be (without limitation) a cetyltrimethylammonium group, a hexadecyltrimethylammonium group, a tetradecyltrimethylammonium group, a dodecyltrimethylammonium group, a lauryl trimethylammonium group, or the like. The anionic subcomponent ($X^-$) of this exemplary alkyltrimethyl ammonium salt might be (without limitation) any of the following ions: bromide, chloride, iodide, hydroxide, nitrate, sulfate, phosphate, formate, acetate, propionate, oxalate, malonate, succinate, or citrate. In certain embodiments, the cationic surfactant is a benzyldimethyl-n-alkylammonium salt, comprising the same group of anions.

The compositions and methods of the invention may further comprise solubilizing agents. Solubilizing agents are particularly useful when the biological sample is resistant to digestion, for example, when the sample comprises whole tissue. In certain embodiments, solubilizing agents help to disassemble the intercellular matrix, allowing the surfactant and protease to more effectively penetrate and disaggregate the sample. Exemplary solubilizing agents include, but are not limited to, 1-methyl-2-pyrolidinone, N-methyl pyrolidinone, pyrolidinone, dimethylsulfoxide, dimethylformamide, and the like.

The invention also provides kits designed for releasing and/or for isolating nucleic acid from biological samples. The kits comprise at least one cationic surfactant and at least one protease, and according to certain embodiments may include additional component(s). In certain embodiments, the kits preferably contain components in pre-measured unit amounts to minimize the measurements by end-users. In certain embodiments, the kits preferably include instructions for performing one or more methods of the invention. Preferably, the kit components are optimized to operate in conjunction with one another.

In certain embodiments, the at least one surfactant comprises CTAB, CTACl, HDTAB, HDTACl, or an equivalent. In certain embodiments, the at least one protease comprises Proteinase K. Optionally, other reagents for isolating extracted nucleic acid may be included in such kits. The kits of the invention may further comprise reaction buffers, salts, ions, stabilizers, nuclease inhibitors, solubilizing agents, or combinations of these components.

The invention, according to certain embodiments, may be better understood by reference to examples. The following examples are intended for illustration purposes only, and should not be construed as limiting the scope of the invention in any way.

EXAMPLE 1

An assay was developed to measure the activity of Proteinase K with BoDipy-labeled Casein Conjugate (Enz Check Protease Assay Kit, Product number E6638; Molecular Probes, Eugene, Oreg.). The concentration of fluorescent BoDipy moieties in this derivatized conjugate is sufficiently high so that when the protein is intact, the fluorescence of individual moieties is quenched. Upon digestion of the derivatized casein by a protease, however, peptides containing a lower number of BoDipy dye molecules are released, resulting in an increase in fluorescence. To determine an initial dynamic range for an assay, BoDipy-labeled Casein was digested for one hour with a decreasing concentration of Proteinase K as follows. Proteinase K (Product number 2546, Ambion) was added over a range of final concentrations (40 µg/ml to 40 µg/mL) to 500 µL of buffer (10 mM Tris, pH 8, 20 mM CaCl$_2$) containing 10 µg/mL BoDipy-labeled Casein Conjugate. Following a one hour incubation at 60° C. with mixing, 100 µL aliquots were transferred to a 96-well optical plate (MicroAmp® Optical 96-Well Reaction Plate, Applied Biosystems, Foster City, Calif.) and the fluorescence was measured in an ABI Prism 7700 spectrophotometer (Applied Biosystems). The background fluorescence was determined by incubating the substrate in buffer without Proteinase K.

As shown in FIG. 1, the amount of fluorescence increased as the Proteinase K concentration increased. The signal appeared to plateau at around 30,000 fluorescence units and released fluorescence was detected from reaction compositions containing as little as 50 ng/mL Proteinase K.

EXAMPLE 2

Initially, a series of reaction compositions were analyzed for their ability to disaggregate a biological sample, e.g., slices of liver. These reaction compositions comprised 100 mM Tris, pH 8.0, 20 mM dithiothreitol (DTT), and optionally, 1 mg/mL Proteinase K, surfactants (e.g., cationic, nonionic and anionic detergents), chaotropes, or the additive 1-methyl-2-pyrollidinone (Sigma). Each reaction compositions was placed in a tube with a slice of liver and then incubated at 65° C. The tubes were observed periodically to determine which reaction compositions were able to efficiently macerate the sample.

As shown in Table 1, Proteinase K alone was able to effectively digest the liver tissue, but only after extended incubation at 65° C. Of all of the reaction compositions examined, those containing the cationic surfactant CTAB most effectively macerated the sample during a one hour incubation period. Additionally, CTAB appeared to enhance the proteolyitic activity of Proteinase K.

TABLE 1

| | 65° C. | | | | | |
|---|---|---|---|---|---|---|
| | No Proteinase K | | | 1 mg/mL Proteinase K | | |
| | 2–5 hr | 16–24 hr | 72 hr | 1 hr | 2–5 hr | 16–24 hr |
| Cationic Surfactants | | | | | | |
| Cetyltrimethylammonium bromide (1%) | | | | 100% | | 100% |
| Cetyltrimethylammonium bromide (0.1%) | | | | 100% | | 100% |
| Nonionic Surfactants | | | | | | |
| Tween 80 (0.1%) | | | | | 0% | 0% |
| Tween 80 (1%) | | | | | 0% | 0% |
| Tween 80 (0.1%) | | | | | 0% | |
| Triton X-100 (0.1%) | | | | | 0% | 0% |
| Triton X-100 (2%) | 0% | 0% | | | | |
| Triton X-100 (1%) | | | | | 30% | 100% |
| Anionic Surfactants | | | | | | |
| Chenodeoxycholic Acid (0.1%) | | | | | 0% | 0% |
| Chenodeoxycholic Acid (1%) | | | | | 0% | 0% |
| Chenodeoxycholic Acid (2%) | | 0% | | | | |
| Cholic Acid (2%) | | 0% | | | | |
| Glycocholic Acid (0.1%) | | | | | 0% | 0% |
| Glycocholic Acid (1%) | | | | | 0% | 0% |
| Taurochenodeoxycholic Acid (0.1%) | | | | | 0% | 0% |
| Taurochenodeoxycholic Acid (1%) | | | | | 0% | 0% |
| Taurocholic Acid (0.1%) | | | | | 0% | 0% |

TABLE 1-continued

| | 65° C. | | | | | |
|---|---|---|---|---|---|---|
| | No Proteinase K | | | 1 mg/mL Proteinase K | | |
| | 2–5 hr | 16–24 hr | 72 hr | 1 hr | 2–5 hr | 16–24 hr |
| Taurocholic Acid (1%) | | | | 0% | | 0% |
| Taurocholic Acid (2%) | | 0% | | | | |
| Taurodeoxycholic Acid (0.1%) | | | | 0% | | 0% |
| Taurodeoxycholic Acid (1%) | | | | 0% | | 0% |
| Octyl sulfonate (2%) | | | 0% | | | |
| Hexane sulfonic acid (2%) | | | 0% | | | |
| Octanonic Acid (2%) | | | 0% | | | |
| SDS (1%) | 0% | | | | 50% | |
| Lauryl Sarcosine (2%) | | 0% | | | | |
| Saponin (0.1%) | | | | 0% | | 0% |
| Saponin (1%) | | | | 0% | | 0% |
| Saponin, (2%) | 0% | 50% | | | | |
| NiaProof Type 8 (0.1%) | | | | 0% | | 0% |
| NiaProof Type 8 (1%) | | | | 0% | | 0% |
| Niaproof Type 8 (2%) | 0% | | | | | |
| Chaotropes | | | | | | |
| Guanidinium chloride (2M) | 0% | | | | 0% | |
| Guanidinium thiocyanate (1M) | 0% | | | | 25% | |
| Tetramethylammonium chloride (0.1M) | | 0% | | 0% | | 0% |
| Tetramethylammonium chloride (1M) | | 0% | | 0% | | 0% |
| Other additives | | | | | | |
| 1-methyl 2-pyrrolidinone (2%) | | 0% | | | | |
| No Additives | | | | | | |
| None | | | | | 0% | 75% |

EXAMPLE 3

To test the effect of cationic surfactants on the activity of Proteinase K, a series of reaction compositions were prepared as follows. Reaction compositions comprised: Casein BoDipy conjugate (1 µg, 10 ng/µL), 10 mM Tris, pH 8, 20 mM $CaCl_2$, 1% surfactant (shown in Table 2 below) and a dilution series of Proteinase K at concentrations of 20 µg/mL, 5 µg/mL, 1.25 µg/mL, 0.31 µg/mL, 0.078 µg/mL, 0.02 µg/mL and 0.005 µg/mL. The anionic surfactant sodium dodecyl sulfate (SDS), known to activate Proteinase K activity under the conditions tested, was included as a positive control. Reaction tubes were incubated at 60° C. in a 96-well optical plate (MicroAmp@ Optical 96-Well Reaction Plate, Applied Biosystems) and the amount of released fluorescence was measured at the indicated time points using an ABI Prism 7700.

TABLE 2

| Surfactants | |
|---|---|
| Surfactant | Source |
| Olealkonium chloride | (CAS No.: 37139-99-4, McIntyre Group LTD). |
| Mackernium SDC-85 (Stearalkonium chloride) | (CAS No. 122-19-0, McIntyre Group LTD). |
| Mackernium NLE | (Quaternium-84) (McIntyre Group LTD) |
| Mackernium 006 | (Polyquaternium-6) (Cas No. 26062-79-3) (McIntyre Group, LTD) |
| Mackernium 007 | (Polyquaternium-7) (Cas No. 26590-05-6) (McIntyre Group, LTD) |
| Mackernium WLE | (Wheat Germamidopropyl Epoxy Q) (McIntyre Group, LTD) |
| Benzalkonium Chloride | (Sigma, Product Number B-6295) |
| Benzyldimethylhexadecylammonium Chloride | (Sigma, Product Number B-4136) |
| Benzyldimethyltetradecylammonium Chloride | (Sigma, Product Number B-5651) |
| Benzyldimethyldodecylammonium bromide | (Sigma, Product Number B-5776) |
| Tetradecyltrimethylammonium Bromide | (Sigma, Product Number T-4762) |
| Hexadecyltrimethylammonium Bromide | (Sigma, Product Number H-5882) |
| Dodecyltrimethylammonium Bromide | (Sigma, Product Number D-8638) |
| Mixed Alkyltrimethylammonium Bromide | (Sigma, Product Number M-7635) |
| Cetyltrimethylammonium bromide (CTAB) | (Calbiochem, Product number B22633) |
| Sodium Dodecyl Sulfate (SDS) | (Sigma, Product Number L6026) |

Figure 2A:
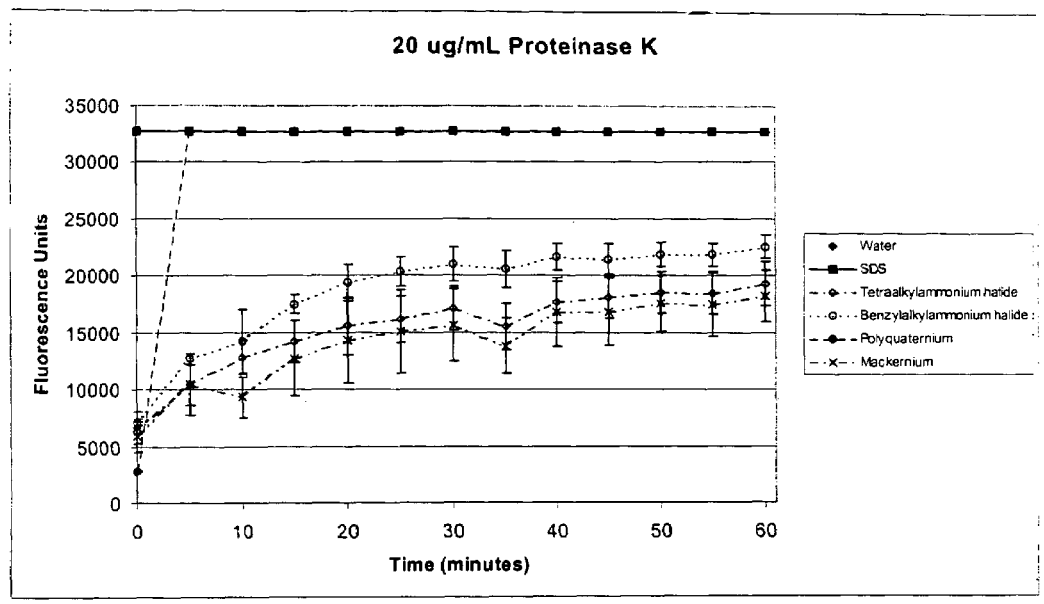
FIG. 2A depicts a reaction composition comprising 20 g/ml Proteinase K.
Figure 2B:
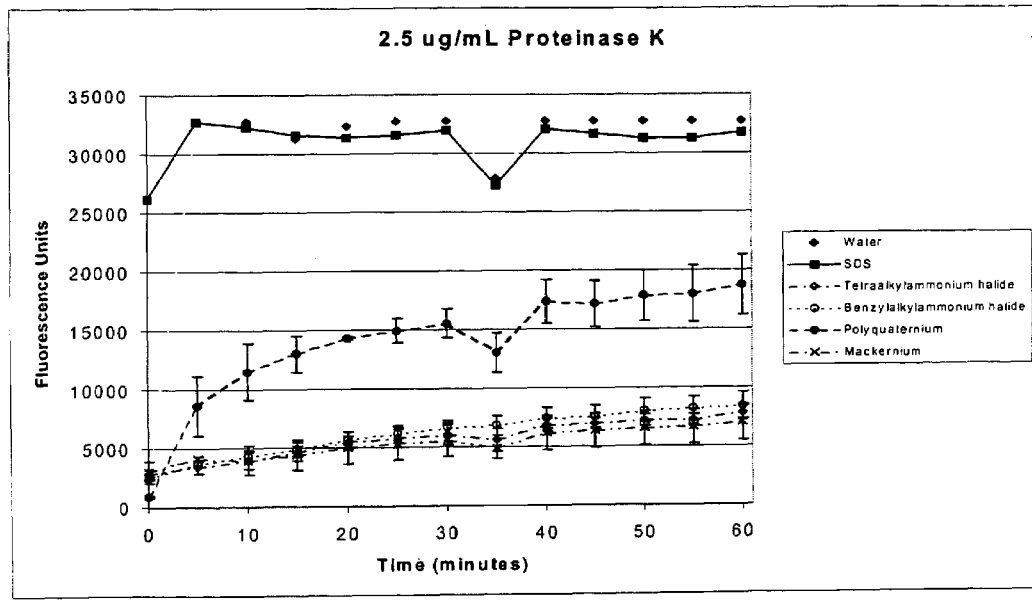
FIG. 2B depicts a reaction composition comprising 2.5 g/ml Proteinase K.
Figure 2C:
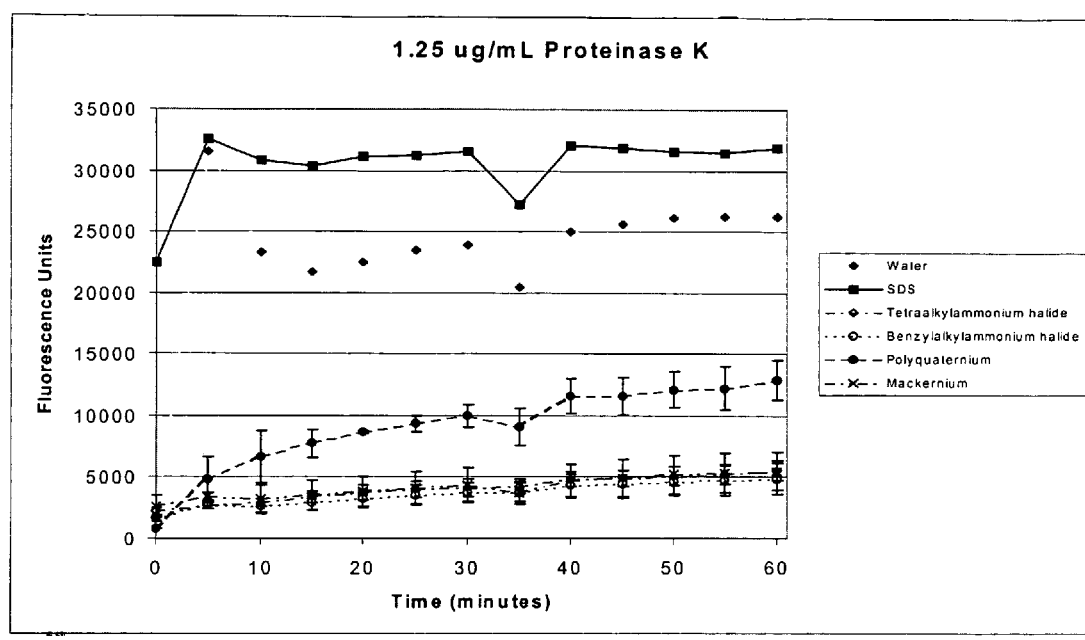
FIG. 2C depicts a reaction composition comprising 1.25 g/ml Proteinase K. The tetraalkylammonium halide symbol (open diamond) represents the average data for the cationic surfactants dodecyltrimethylammonium bromide, tetradecyltrimethylammonium bromide, hexadecyltrimethylammonium bromide, cetyltrimethylammonium bromide, and mixed alkyltrimethylammonium bromide. The symbol for benzylalkylammonium halide (open circle) represents the average data for the cationic surfactants benzalkonium chloride, benzyldimethyldodecylammonium bromide, benzyldimethylhexadecylammonium bromide and benzyldimethyltetradecyl ammonium chloride. The symbol for Mackernium (X) represents the average data for the cationic surfactants Mackernium SDC-85, Mackernium KP, Mackernium WLE and Mackernium NLE. The polyquaternium symbol (closed circle) represents the average data for the cationic polymers Mackernium 006 and Mackernium 007. The results obtained using water (closed diamond) and using the anionic surfactant SDS (closed square) are also shown. The error bars represent the standard deviation for the each data set.

As shown in FIGS. 2A–C: (i) Proteinase K without surfactant has high proteolytic activity, even at ambient temperature (see 0 minutes incubation in water); (ii) SDS enhances the activity of Proteinase K on the casein substrate; (iii) the two cationic polymers (Mackernium 006 and 007) have a slightly inhibitory activity on Proteinase K activity; and (iv) all of the cationic surfactants tested appear to inhibit Proteinase K activity (compare the tetraalkylammonium halide, benzylalkylammonium halide, or polyquaterniums curve with that for water alone, i.e., no surfactant).

EXAMPLE 4

Since it is typically difficult to extract nucleic acid from whole tissue, it can be used effectively to illustrate the efficiency of the compositions and methods of the invention. Thus, the remainder of the examples were performed using liver tissue as an exemplary whole tissue. The skilled artisan will understand, however, that the disclosed compositions and methods may also be effectively employed using a broad range of biological samples and that the invention is not to be limited to use with any sample type.

In the initial approach for evaluating the efficacy of nucleic acid release by various test treatments, liver samples were digested for a specified period of time in reaction compositions comprising surfactant and Proteinase K. The protocol included removing undigested material using centrifugation. Preliminary results using purified nucleic acid and cationic surfactants demonstrated that the cationic surfactant was forming a precipitate with the nucleic acid (data not shown). Further, this complex was being removed with the undigested tissue during centrifugation. Thus, one way to quantify the amount of nucleic acid being released from the sample, included freeing the nucleic acid from the surfactant:nucleic acid complex. Conditions were evaluated for freeing the nucleic acid from the cationic surfactant complexes as follows.

Calf thymus DNA (Sigma; 700 µg/mL lightly sheared using an 18 gauge hypodermic needle) was mixed with 1% CTAB in 100 mM Tris, pH 8 to form a reaction composition. Initially, a noticeable precipitate was observed. A variety of additives, shown in Table 3, were tested with aliquots of this reaction composition to identify compositions that would solubilize the cationic surfactant:nucleic acid precipitate.

TABLE 3

| Sample | Additive (final concentration) | Result |
| --- | --- | --- |
| 1 | 91 mM NaCl | Nucleic acid precipitated |
| 2 | 333 mM NaCl | Nucleic acid precipitated |
| 3 | 117 mM Tetramethylammonium chloride | Nucleic acid precipitated |
| 4 | 758 mM Tetramethylammonium chloride | Nucleic acid precipitated |
| 5 | 95 mM Tetrabutylammonium chloride | Nucleic acid precipitated |
| 6 | 400 mM Tetrabutylammonium chloride | Nucleic acid precipitated |
| 7 | 312.5 mM NaCl, 6.25% 1-Methyl-2-Pyrrolidinone | Nucleic acid precipitated |
| 8 | 692 mM Tetramethylammonium chloride, 7.5% 1-Methyl-2-pyrrolidinone | Nucleic acid precipitated |
| 9 | 370 mM Tetrabutylammonium chloride, 7.4% 1-Methyl-2-pyrrolidinone | Nucleic acid precipitated |
| 10 | 9.1% 1-Methyl-2-pyrrolidinone (Sigma #M-6762) | Nucleic acid precipitated |
| 11 | 294 mM NaCl, 5.9% 1-Methyl-2-Pyrrolidinone, 5.9% Tween 20 | Nucleic acid pellet fairly dissolved |
| 12 | 643 mM Tetramethylammonium chloride, 7.0% 1-Methyl-2-pyrrolidinone, 7.0% Tween 20 | Nucleic acid pellet fairly dissolved |
| 13 | 345 mM Tetrabutylammonium chloride, 6.9% 1-Methyl-2-Pyrrolidinone, 6.9% Tween 20 | Nucleic acid pellet began to solubilize |
| 14 | 8.3% 1-Methyl-2-Pyrrolidinone, 8.3% Tween 20 | Nucleic acid pellet began to solubilize |
| 15 | 10% Tween 20 (Sigma #P-9416) | Nucleic acid precipitated |
| 16 | 312.5 mM NaCl, 6.25% Tween 20 | Nucleic acid pellet completely solubilized |
| 17 | 2.0% Tween 20 | Nucleic acid precipitated |
| 18 | 160 mM NaCl, 1.6% Tween 20 | Nucleic acid precipitated |
| 19 | 9.1% 1-hexanesulfonic acid | Nucleic acid pellet partially solubilized |
| 20 | 17% 1-hexanesulfonic acid | Nucleic acid pellet partially solubilized |
| 21 | 200 mM NaCl, 16% Hexane sulfonic acid | Nucleic acid pellet partially solubilized |
| 22 | 9.1% Decanesulfonic acid | Nucleic acid pellet partially solubilized |
| 23 | 217 mM NaCl, 8.7% Decanesulfonic acid | Nucleic acid pellet partially solubilized |
| 24 | 50% Nucleic Acid Purification Lysis Solution | Nucleic acid pellet completely solubilized |
| 25 | 33% Nucleic Acid Purification Lysis Solution | Nucleic acid pellet completely solubilized |
| 26 | 23% Nucleic Acid Purification Lysis Solution | Nucleic acid pellet partially solubilized |
| 27 | 297 mM NaOAc | Nucleic Acid precipitated |
| 28 | 292 mM NaOAc, 1.8% Tween 20 | Nucleic Acid precipitated |
| 29 | 313 mM NaOAc, 2.6% Tween 20 | Nucleic Acid precipitated |
| 30 | 535 mM NaCl, 1.75% Tween 20 | Nucleic acid pellet completely solubilized |

As shown in Table 3, four of the reaction compositions resulted in complete solubilization of the precipitate. Nucleic Acid Purification Lysis Solution (# 4305895, Applied Biosystems), used at final concentrations of 33% or 50%, completely solubilized the precipitate (see samples 24–25). Additionally, some combinations of the salt NaCl and the nonionic detergent Tween 20 completely solubilized the precipitate (see samples 16 and 30). However, neither NaCl nor Tween 20, used alone, solubilized the precipitate (see samples 1, 2, 15, and 17). The skilled artisan will understand that additional combinations of salts and nonionic surfactants used at varying concentrations can be used to dissolve the cationic surfactant:nucleic acid precipitates.

EXAMPLE 5

To evaluate the ability of various cationic surfactants to increase the digestion of tissue by Proteinase K, liver slices were digested using reaction compositions including one of the sixteen surfactants (shown in Table 4), both with and without Proteinase K. The reducing agent dithiothreitol (DTT) was included to evaluate the effect of reducing conditions on tissue digestion. Liver tissue (80–120 mg) was placed into each of thirty-four Eppendorf tubes (seventeen pairs of tubes) containing 1000 µL of 10 mM Tris, pH 8, 20 mM $CaCl_2$, and 20 mM dithiothreitol. One of the sixteen surfactants was added to one pair of tubes to yield a final concentration of 1% surfactant. The seventeenth pair of tubes served as non-surfactant controls. One milligram (mg) of Proteinase K was added to one tube of each of the seventeen pairs. The thirty-four tubes were then incubated at 60° C. with mixing (Eppendorf Thermomixer, Model 5436).

TABLE 4

| Surfactant | Chemical Formula |
| --- | --- |
| SDS | $CH_3(CH_2)_{11}OSO_3Na$ |
| Mackernium KP | $R_1R_2(CH_3)_2NCl$ $R_1$ = fatty group, $R_2$ = benzyl, methyl or epoxy group |

TABLE 4-continued

| Surfactant | Chemical Formula |
|---|---|
| Mackernium WLE | $R_1R_2(CH_3)_2NCl$ $R_1$ = fatty group, $R_2$ = benzyl, methyl or epoxy group |
| Benzalkonium chloride | $C_6H_5CH_2N(CH_3)_2RCl$ $R = C_8H_{17}$ to $C_{18}H_{37}$ |
| Mackernium 006 | Polyquaternium |
| Mackernium 007 | Polyquaternium |
| Mackernium NLE | $R_1R_2(CH_3)_2NCl$ $R_1$ = fatty group, $R_2$ = benzyl, methyl or epoxy group |
| Mackernium SDC-85 | $R_1R_2(CH_3)_2NCl$ $R_1$ = fatty group, $R_2$ = benzyl, methyl or epoxy group |
| Dodecyltrimethylammonium bromide | $CH_3(CH_2)_{11}N(CH_3)_3Br$ |
| Tetradecyltrimethylammonium bromide | $CH_3(CH_2)_{13}N(CH_3)_3Br$ |
| Hexadecyltrimethylammonium bromide | $CH_3(CH_2)_{15}N(CH_3)_3Br$ |
| CTAB | $CH_3(CH_2)_{15}N(CH_3)_3Br$ |
| Mixed alkyltrimethylammonium bromide | $CH_3(CH_2)_nN(CH_3)_3Br$ |
| Benzyldimethyldodecylammonium bromide | $C_6H_5CH_2N[(CH_2)_{11}CH_3](CH_3)_2Br$ |
| Benzyldimethyltetradecyl ammonium chloride | $C_6H_5CH_2N[(CH_2)_{13}CH_3](CH_3)_2Cl$ |
| Benzyldimethylhexadecylammonium bromide | $C_6H_5CH_2N[(CH_2)_{15}CH_3](CH_3)_2Br$ |

Each tube was visually evaluated after 15 minutes and 52 minutes of incubation.

The results, shown in Table 5 (fifteen minutes incubation) and Table 6 (fifty-two minutes incubation), indicate that under the conditions tested, the combination of CTAB and Proteinase K caused total disaggregation of the tissue sample at either time point.

Notably, CTAB alone caused no apparent sample disaggregation. The presence of DTT did not seem to significantly effect tissue disaggregation under these conditions.

TABLE 5

Observations after Fifteen Minutes Incubation.

| Surfactant | PK | Tissue Disaggregation | Color of Composition |
|---|---|---|---|
| Buffer alone (control) | Y | 0 | Light pink |
| SDS | Y | 3 | Slightly Cloudy |
| Mackernium KP | Y | 1 | Slightly Cloudy |
| Mackernium WLE | Y | 0 | Clear |
| Benzalkonium chloride | Y | 1 | Slightly Cloudy |
| Mackernium 006 | Y | 1 | Slightly Cloudy |
| Mackernium 007 | Y | 2 | Slightly Cloudy |
| Mackernium NLE | Y | 1 | Slightly Cloudy |
| Dodecyltrimethylammonium bromide | Y | 2 | Medium Cloudy |
| Tetradecyltrimethylammonium bromide | Y | 0 | Clear |
| Hexadecyltrimethylammonium bromide | Y | 0 | Clear |
| CTAB | Y | 4 | Dark brown |
| Mackernium SDC-85 | Y | 3 | Medium cloudy |
| Mixed alkyltrimethylammonium bromide | Y | 3 | Medium cloudy |
| Benzyldimethyldodecylammonium bromide | Y | 0 | Clear |
| Benzyldimethylhexadecylammonium bromide | Y | 0 | Clear |
| Benzyldimethyltetradecyl ammonium chloride | Y | 0 | Clear |
| Buffer alone (control) | N | 0 | Pink |
| SDS | N | 0 | Slightly cloudy |
| Mackernium KP | N | 0 | Clear |
| Mackernium WLE | N | 0 | Pink |
| Benzalkonium chloride | N | 0 | Clear |
| Mackernium 006 | N | 0 | Slightly pink |
| Mackernium 007 | N | 0 | Slightly pink |
| Mackernium NLE | N | 0 | Slightly brown |
| Dodecyltrimethylammonium bromide | N | 0 | Slightly pink |
| Tetradecyltrimethylammonium bromide | N | 0 | Slightly pink |
| Hexadecyltrimethylammonium bromide | N | 0 | Clear |
| CTAB | N | 0 | Slightly pink |
| Mackernium SDC-85 | N | 0 | Clear |
| Mixed alkyltrimethylammonium bromide | N | 0 | Clear |
| Benzyldimethyldodecylammonium bromide | N | 0 | Slightly cloudy |
| Benzyldimethylhexadecylammonium bromide | N | 0 | Clear |
| Benzyldimethyltetradecyl ammonium chloride | N | 0 | Clear |

PK = presence or absence of Proteinase K in the reaction composition; Y = Proteinase K was present; N = Proteinase K was not present in the reaction composition.
Tissue disaggregation: 0 = none; 1 = No fragmentation, supernatant slightly cloudy; 2 = Little fragmentation, supernatant slightly cloudy; 3 = More significant tissue supernatant, supernatant very cloudy; 4 = complete tissue aggregation with little insoluble material remaining.

TABLE 6

Observations after Fifty-Two Minutes Incubation.

| Surfactant | PK | Tissue Disaggregation | Color of Composition |
|---|---|---|---|
| Buffer alone (control) | Y | 0 | Slightly brown |
| SDS | Y | 3 | Moderately cloudy |
| Mackernium KP | Y | 4 | Very cloudy |
| Mackernium WLE | Y | 2 | Medium cloudy |
| Benzalkonium chloride | Y | 2 | Medium cloudy |
| Mackernium 006 | Y | 0 | Slightly brown |
| Mackernium 007 | Y | 2 | Some cloudiness |
| Mackernium NLE | Y | 1 | Slightly cloudy |
| Dodecyltrimethylammonium bromide | Y | 3 | Medium cloudy |
| Tetradecyltrimethylammonium bromide | Y | 1 | Slightly brown |
| Hexadecyltrimethylammonium bromide | Y | 1 | Medium brown |
| CTAB | Y | 4 | Very brown, milky |
| Mackernium SDC-85 | Y | 3 | Very cloudy |
| Mixed alkyltrimethylammonium bromide | Y | 3 | Very cloudy |
| Benzyldimethyldodecylammonium bromide | Y | 1 | Slightly cloudy |
| Benzyldimethylhexadecylammonium bromide | Y | 1 | Slightly cloudy |
| Benzyldimethyltetradecyl ammonium chloride | Y | 1 | Slightly cloudy |
| Water | N | 0 | Slightly brown |
| SDS | N | 0 | Slightly pink |
| Mackernium KP | N | 0 | Clear |
| Mackernium WLE | N | 0 | Slightly brown |
| Benzalkonium chloride | N | 0 | Clear |
| Mackernium 006 | N | 0 | Slightly brown |
| Mackernium 007 | N | 0 | Slightly cloudy |
| Mackernium NLE | N | 0 | Clear |
| Dodecyltrimethylammonium bromide | N | 0 | Clear |

TABLE 6-continued

Observations after Fifty-Two Minutes Incubation.

| Surfactant | PK | Tissue Dis-aggregation | Color of Composition |
|---|---|---|---|
| Tetradecyltrimethylammonium bromide | N | 0 | Clear |
| Hexadecyltrimethylammonium bromide | N | 0 | Slightly brown |
| CTAB | N | 0 | Slightly brown |
| Mackernium SDC-85 | N | 0 | Slightly pink |
| Mixed alkyltrimethylammonium bromide | N | 0 | Clear |
| Benzyldimethyldodecylammonium bromide | N | 0 | Slightly brown |
| Benzyldimethylhexadecylammonium bromide | N | 0 | Clear |
| Benzyldimethyltetradecyl ammonium chloride | N | 0 | Clear |

See legend to Table 5 for explanation of nomenclature.

EXAMPLE 6

To examine the ability of cationic surfactants and Proteinase K to release high integrity nucleic acids from a biological sample, the released nucleic acid was isolated. Slices of liver tissue (90–200 mg per slice) were placed into each of twenty-two Eppendorf microfuge tubes. Four hundred µL of 50 mM Tris, pH 8, 20 mM $CaCl_2$, 1% surfactant, and 1 mg Proteinase K was added to each tube. The tubes were incubated at 60° C. for 22 minutes with mixing (Eppendorf Thermomixer, Model 5436).

Following the incubation, Nucleic Acid Purification Lysis Solution (# 4305895, Applied Biosystems; final concentration 29%), sodium acetate (final concentration 214 mM) and glycogen (Mussel type VII, Sigma; final concentration 143 µg/mL) was added to each tube to dissolve the surfactant: nucleic acid complexes. The tubes were centrifuged in an Eppendorf microfuge (Model 5415C) at 14,000 RPM for 5 minutes to pellet remaining tissue fragments. The resulting supernatant was extracted using 700 µL of phenol (Sigma) saturated with 10 mM Tris HCl, pH 8.0, and 1 mM EDTA (saturated phenol). The pelleted material was also extracted with saturated phenol to obtain nucleic acid if any remained in the undigested sample. The extracted nucleic acid was precipitated using an equal volume (750 µL) of 2-propanol, and the tubes were incubated at −20° C. for 3 hours. The samples were centrifuged at ambient temperature in a microfuge at 14,000 RPM for 5 minutes, as before, to pellet the nucleic acid. The nucleic acid pellets were washed with 1 mL of 70% ethanol and the samples were centrifuged at ambient temperature in a microfuge at 14,000 RPM for 5 minutes. The washed nucleic acid pellets were resuspended in 100 µL 10 mM Tris, pH 8, 0.1 mM EDTA, and 1 unit/µL RNasin. The amount of released nucleic acid was quantitated using a UV/Vis Spectrophotometer (Hewlett Packard, Model 8453). For quantitation purposes, it was assumed that the material that absorbed UV light at a wavelength of 260 nm was nucleic acid. Thus, an extinction coefficient of 1 $OD_{260}$=40 µg/mL was used.

Figure 3:
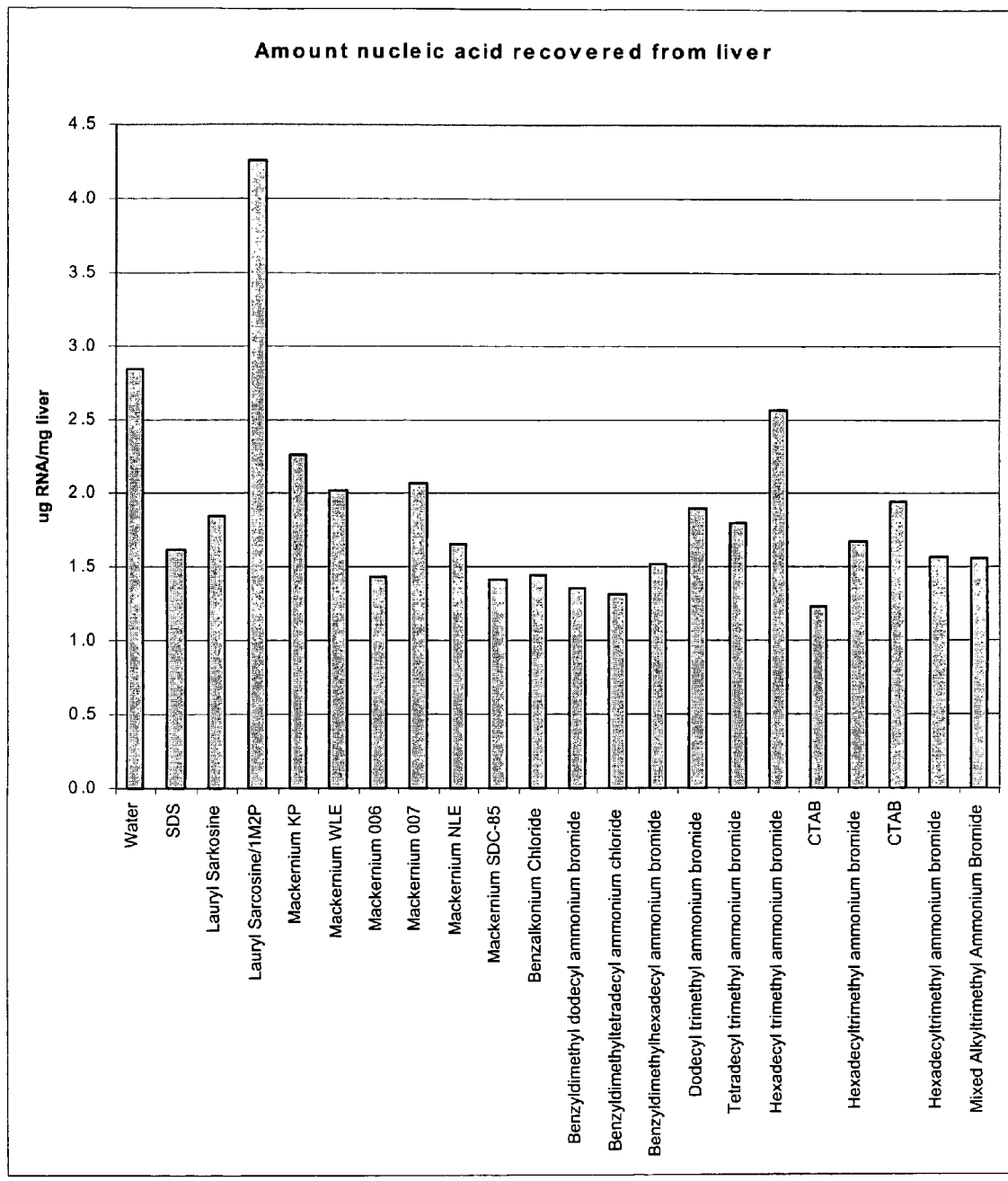
FIG. 3: illustrates the quantity of nucleic acid, measured in g of nucleic acid/mg of sample, released using reaction compositions comprising Proteinase K and various surfactants.

FIG. 3 shows the amount of $A_{260}$-absorbing material recovered from the sample (µg nucleic acid/mg tissue processed). The results were normalized for the weight of each sample. Despite the reduced proteolytic activity of Proteinase K in the presence of the cationic surfactants, as demonstrated in the previous example, the amount of $A_{260}$-absorbing material was similar to the amount obtained with the anionic surfactants or without surfactant.

To evaluate the integrity of the released nucleic acid (i.e., its degree of degradation), and the amount of nucleic acid remaining in the tissue pellet, one tenth of each sample was analyzed by electrophoresis on a 1% agarose gel according to standard molecular biology procedures. Descriptions of standard molecular biology procedures may be found, among other places, in Molecular Cloning: A Laboratory Manual, Sambrook et al., 1989, Cold Spring Harbor Press, Cold Spring Harbor, N.Y.; Current Protocols in Molecular Biology, Ausbel et al., 1993 and supplements through September 2000, John Wiley & Sons, New York, N.Y.; or Molecular Biology Techniques, W. Ream et al., Academic Press, San Diego, Calif., 1999.

Figure 4:
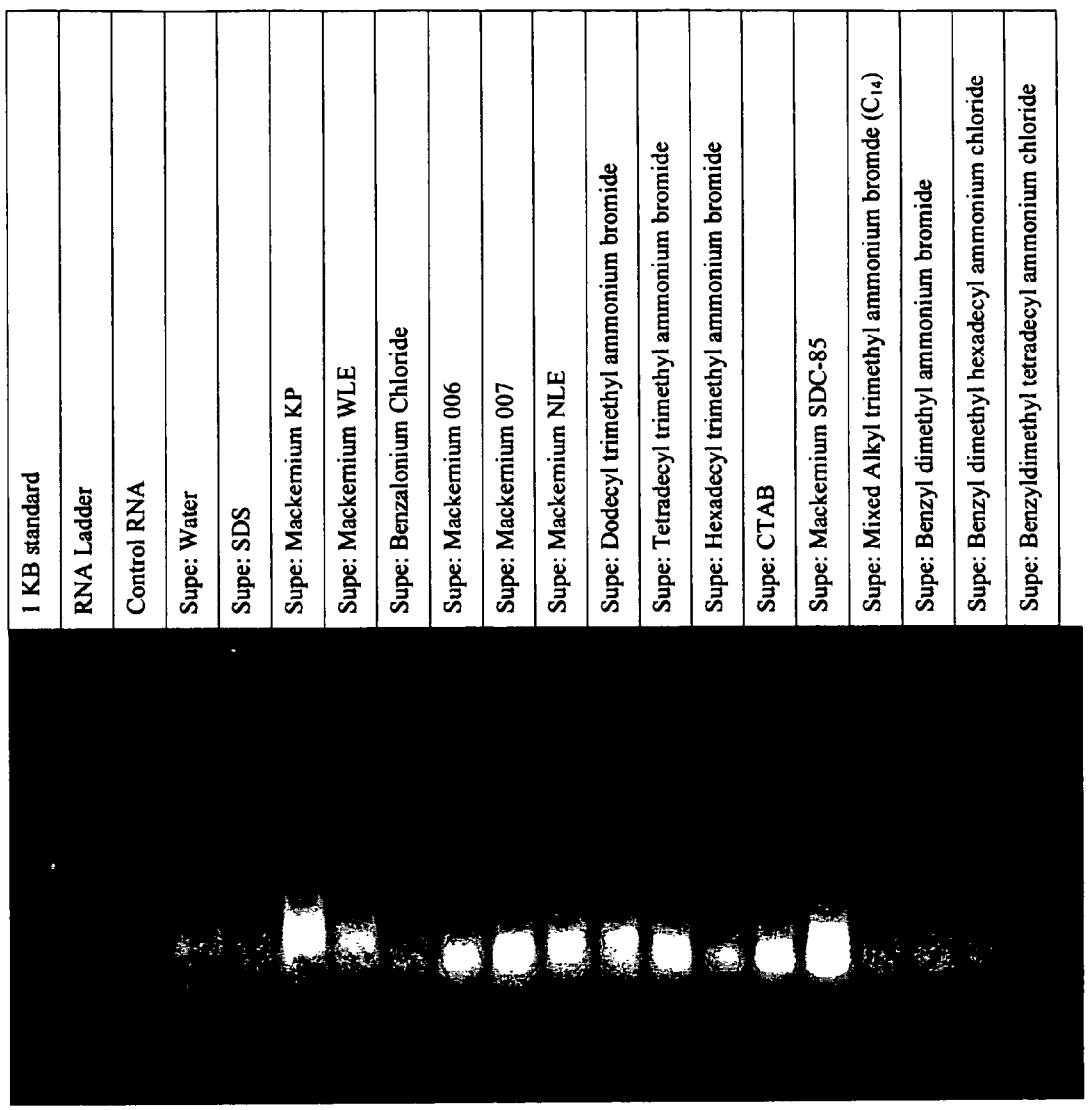
FIG. 4: depicts a stained agarose gel that provides a comparison between the amount of nucleic acid that is released (supe) with the nucleic acid remaining in the sample (pellet) following incubation with the reaction compositions comprising the indicated surfactants.
Figure 4:
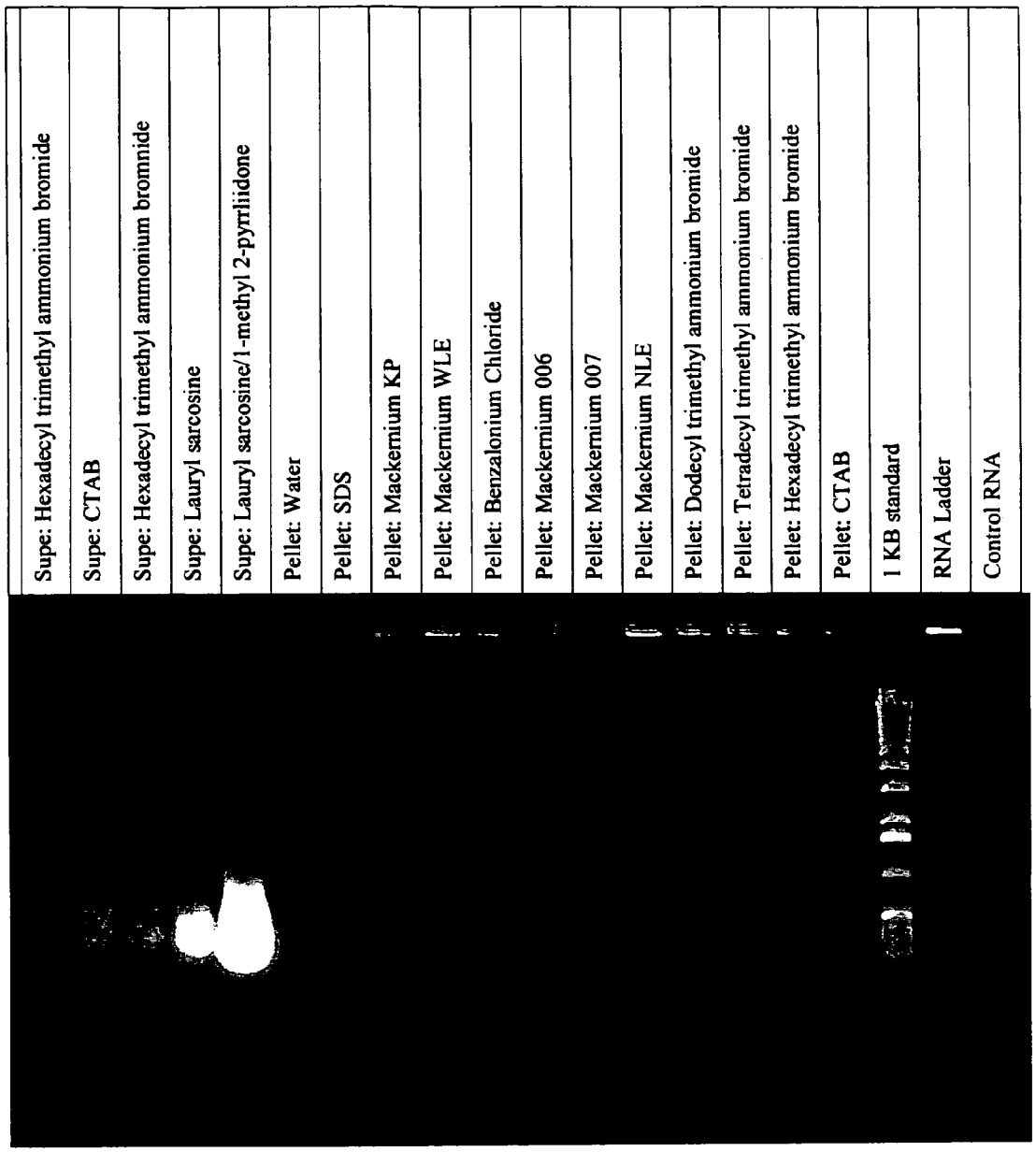

As shown in FIG. 4, most of the cationic surfactant: Proteinase K combinations released nucleic acid as evidenced by the little nucleic acid that remained in the pellet. The released nucleic acid was observed to have a high electrophoretic mobility, since it appeared near the bottom of the gel. Since intact, high integrity nucleic acid typically has a low, rather than a high, electrophoretic mobility, the recovered nucleic acid apparently was highly fragmented using these conditions. In other words, it apparently had a low integrity.

EXAMPLE 7

The results from Example 6 indicate that there was significant nuclease activity present in the sample. To reduce the nucleolytic activity of endogenous RNAses, the pH of the reaction composition was lowered to approximately 6.0 and the incubation temperature was decreased to 45° C. Several additives, including phenylglyoxal (Aldrich #14243-3), 1-methyl-2-pyrolidinone, RNA Later (Ambion, #7020), and Streck Tissue Fixitive (Streck Laboratories, #265138) were also tested to evaluate their effect on endogenous RNAse activity in these reaction compositions. Phenylglyoxal is known to reduce ribonuclease activity (see Takahashi, The Structure And Function Of Ribonuclease $T_1$. XI. Modification Of The Single Arginine Residue In Ribonuclease T1 By Phenylglyoxal And Glyoxal, J. Biochem (Japan) 68:659–664, 1970). The product literature for RNA Later claims that the reagent stabilizes RNA in tissue and Streck Tissue Fixative is believed to preserve the integrity of tissue.

Slices of liver tissue (100–200 mg/sample) were placed into nineteen Eppendorf tubes. Four hundred microliters of a reaction composition comprising 100 mM MES (Sigma #M-5287), pH 6, 20 mM $CaCl_2$, and 1 mg Proteinase K, was added to each tube. Additional components, including anionic surfactants (SDS, Sarkosyl) and cationic surfactants (CTAB, CTACI, and tetramethyl ammonium chloride) were added to specific tubes, as shown in Table 7.

TABLE 7

| Tube # | Additional Reaction Composition Components |
|---|---|
| 1 | No additional components (control) |
| 2 | 1% Sodium Dodecyl Sulfate (SDS) |
| 3 | 1% SDS, 10% 1-Methyl-2-pyrolidinone |
| 4 | 1% SDS, 100 mM Phenylglyoxal |
| 5 | 1% SDS, 80% RNA Later |
| 6 | 1% SDS, 80% Streck Tissue Fixative |
| 7 | 1% Cetyltrimethylammonium bromide (CTAB) |
| 8 | 1% CTAB, 10% 1-Methyl-2-pyrolidinone |
| 9 | 1% CTAB, 100 mM Phenylglyoxal |

TABLE 7-continued

| Tube # | Additional Reaction Composition Components |
|---|---|
| 10 | 1% CTAB, 80% RNA Later |
| 11 | 1% CTAB, 80% Streck Tissue Fixative |
| 12 | 1% Sarkosyl |
| 13 | 1% Sarkosyl, 10% 1-Methyl-2-pyrolidinone |
| 14 | 1% Sarkosyl, 10 mM Phenylglyoxal |
| 15 | 1% Sarkosyl, 80% RNA Later |
| 16 | 1% Sarkosyl, 80% Streck Tissue Fixative |
| 17 | 1% Cetyltrimethylammonium chloride (CTACl) |
| 18 | 600 mM Tetrabutylammonium chloride |
| 19 | 800 mM Tetramethylammonium chloride |

The tubes were incubated at 45° C. for 20 minutes with mixing (Eppendorf Thermomixer, Model 5436). Following the incubation, 171 μL of a solution containing 1.75 M NaCl, 29% Tween 20, 585 μg/mL glycogen (447 mM NaCl, 7.5% Tween 20, and 149 μg/mL glycogen) was added to each tube to dissolve the surfactant:nucleic acid complex. Glycogen served as a nucleic acid carrier. Undigested tissue fragments were removed by centrifugation using the methods the same as or similar to those discussed in Example 6. The supernatant was phenol extracted (saturated with 10 mM Tris HCl, pH 8, 1 mM EDTA; Sigma # P-4557), isopropanol precipitated (Aldrich #19076-4), and ethanol washed using methods the same as or similar to those described in Example 6. The washed nucleic acid pellets were resuspend with 100 μL 10 mM Tris, pH 8.0, 0.1 mM EDTA, and 1 unit/μL Rnasin. The amount of nucleic acid released and its integrity were evaluated as described in Example 6.

Figure 5:
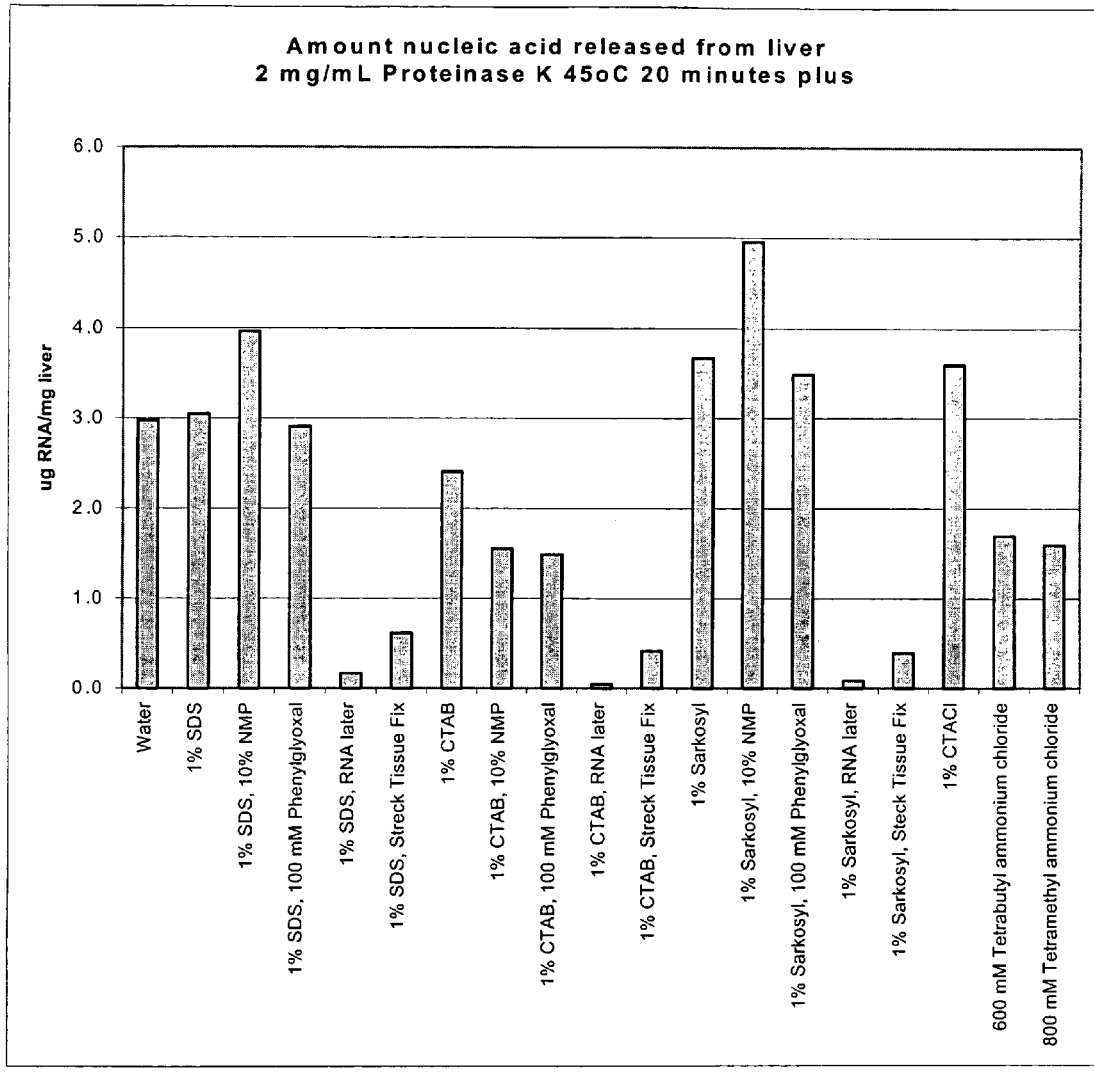
FIG. 5: illustrates the quantity of nucleic acid that is released and isolated from liver slices incubated for 20 minutes at 45° C. in reaction compositions comprising 2 mg/mL Proteinase K and the indicated surfactants. When used in these figures, NMP is 1-methyl-2-pyrolidinone.
Figure 6:
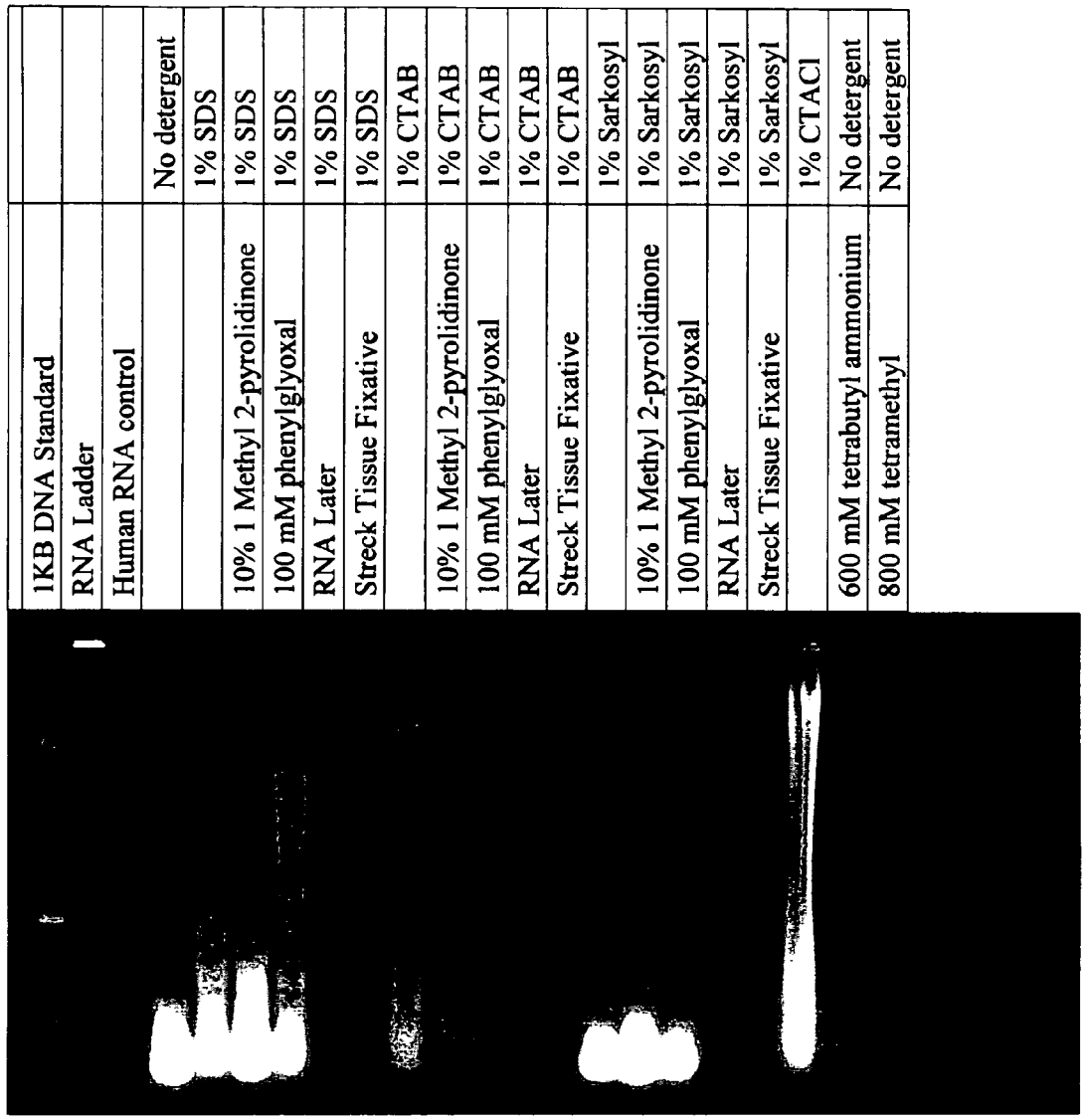
FIG. 6: depicts an ethidium bromide stained agarose gel that demonstrates the quality (integrity) of the released and isolated nucleic acid of FIG. 5.

As shown in FIG. 5, under these conditions, Proteinase K combined with either of the cationic surfactants (CTAB and CTACl) or the anionic surfactants (SDS and Sarkosyl) released $A_{260}$ absorbing material from the sample. When either Streck Tissue Fixative or RNA Later was added to these reactions, very little-$A_{260}$ absorbing material was released. The average molecular weight for the released nucleic acid was typically higher when Proteinase K digestion was carried out at the lower pH and temperatures (compare FIG. 4 to FIG. 6). Additionally, the average molecular weight for the released nucleic acid was typically higher when Proteinase K digestion was performed in the presence of the cationic surfactants (compare Lanes 5–9 and 15–19 to 10–14 in FIG. 6).

EXAMPLE 8

To compare CTACl to CTAB, those two surfactants were evaluated in parallel along with hexadecyltrimethylammonium bromide (HDTAB), hexadecyltrimethylammonium chloride (HDTACl), and Sarkosyl. Three additives, phenylglyoxal, acridine orange (e.g., Sigma #A6014), and 1-methyl-2-pyrrolidinone, were also evaluated. Phenylglyoxal was tested to determine if it would reduce RNAse activity. Acridine Orange, a dye compound known to interact with nucleic acid molecules, was tested to determine if it would reduce nuclease activity. 1-Methyl-2-pyrrolidinone was tested to see if it would enhance solubility of the sample by various reaction compositions.

Slices of liver tissue (100–200 mg/sample) were placed into twenty-one Eppendorf tubes. Four hundred microliters of a reaction composition, comprising 100 mM MES, pH 6, 20 mM $CaCl_2$, and 1 mg Proteinase K, was added to each tube. Additional components were added to specific tubes, as shown in Table 8.

TABLE 8

| Tube # | Additional Reaction Composition Components |
|---|---|
| 1 | 1% Cetyltrimethylammonium Bromide (CTAB) |
| 2 | 1% CTAB, 100 mM Phenylglyoxal |
| 3 | 1% CTAB, 10% 1-Methyl-2-pyrolidinone |
| 4 | 1% CTAB, 200 μg/mL Acridine orange |
| 5 | 1% Cetyltrimethylammonium Chloride (CTACl) |
| 6 | 1% CTACl, 100 mM Phenylglyoxal |
| 7 | 1% CTACl, 10% 1-Methyl-2-pyrolidinone |
| 8 | 1% CTACl, 200 μg/mL Acridine orange |
| 9 | 1% Hexatrimethylammonium Bromide (HTMAB) |
| 10 | 1% HTMAB, 100 mM Phenylglyoxal |
| 11 | 1% HTMAB, 10% 1-Methyl-2-pyrolidinone |
| 12 | 1% HTMAB, 200 μg/mL Acridine orange |
| 13 | 1% Hexatrimethylammonium Chloride (HTMACl) |
| 14 | 1% HTMACl, 100 mM Phenylglyoxal |
| 15 | 1% HTMACl, 10% 1-Methyl-2-pyrolidinone |
| 16 | 1% HTMACl, 200 μg/mL Acridine orange |
| 17 | 1% Sarkosyl (N-lauryl sarcosine) |
| 18 | 1% Sarkosyl, 100 mM Phenylglyoxal |
| 19 | 1% Sarkosyl, 10% 1-Methyl-2-pyrolidinone |
| 20 | 1% Sarkosyl, 200 μg/mL Acridine orange |
| 21 | No additives |

The tubes were incubated at 45° C. for 30 minutes with mixing (Eppendorf Thermomixer, Model 5436). Surfactant:protease complexes were solubilized using methods the same as or similar to those described in Example 7. Remaining tissue fragments were removed by centrifugation using methods the same as or similar to those described in Example 7. The supernatant was phenol extracted, isopropanol precipitated, and ethanol washed using methods the same as or similar to those described in Example 6. The washed nucleic acid pellets were resuspended and the amount and the integrity of the released nucleic acid were evaluated using methods the same as or similar to those described in Example 6.

Figure 7:
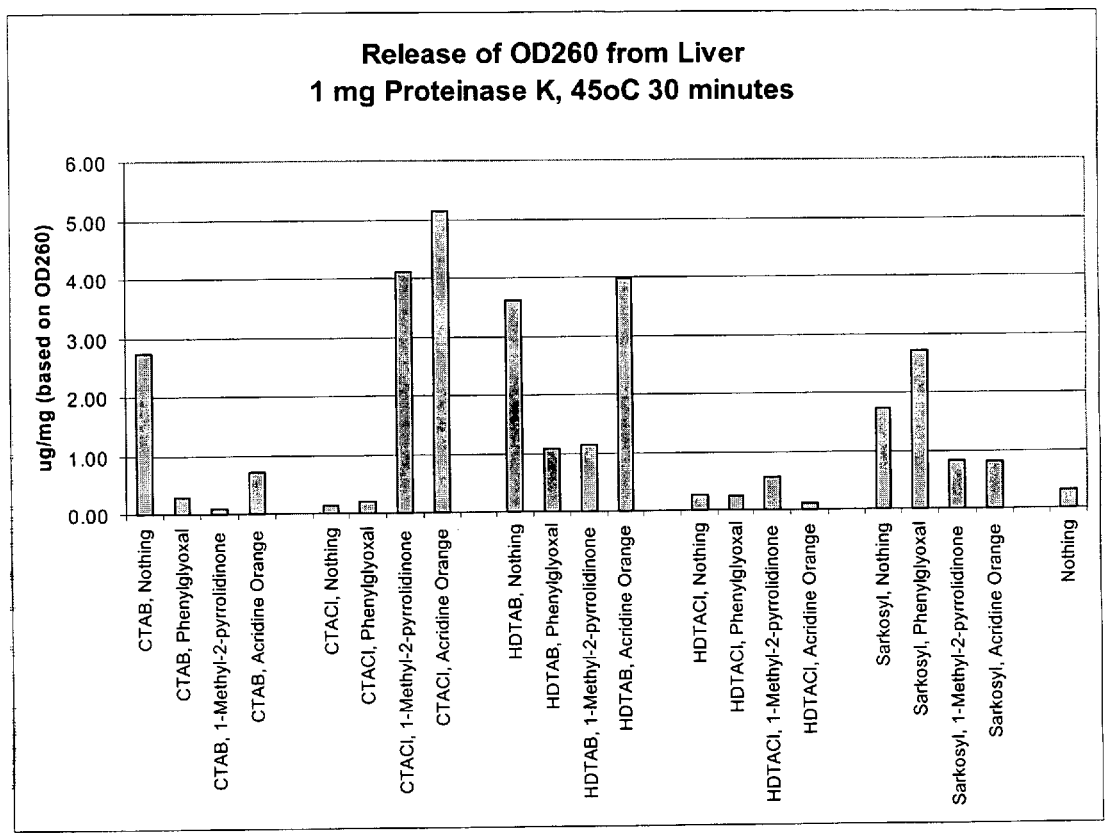
FIG. 7: illustrates the quantity of nucleic acid that is released and isolated from liver slices incubated for 30 minutes at 45° C. in reaction compositions comprising 1 mg/mL Proteinase K and the indicated surfactants and additives. When used in these figures, "nothing" means no additional reagent was added.

As shown in FIG. 7, the effect of the three additives varied depending on the surfactant. For example, the amount of nucleic acid released using CTACl and 1-methyl-2-pyrolidinone was greater in comparison with a composition of CTACl without an additive. However, the amount of nucleic acid released using HDTAB and 1-methyl-2-pyrolidinone was less in comparison with a composition of HDTAB without an additive.

Figure 8:
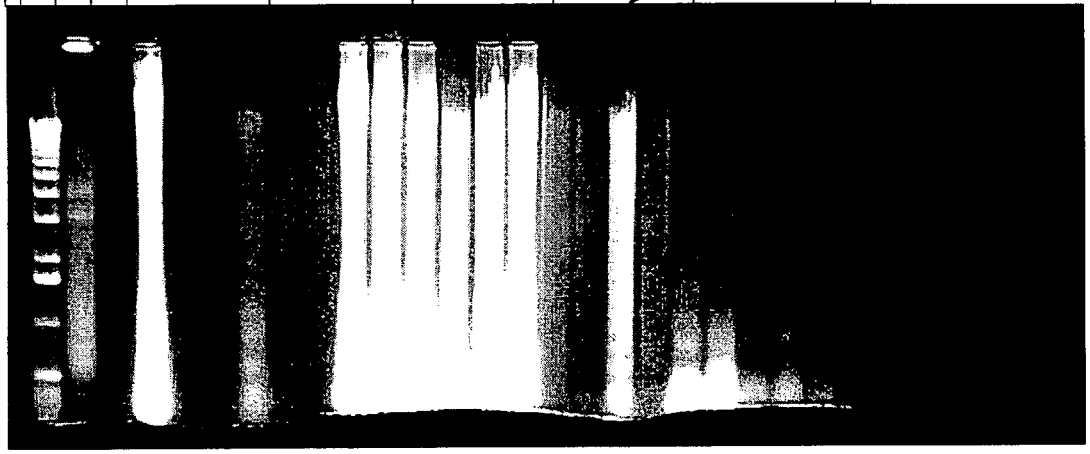
FIG. 8: depicts an ethidium bromide stained agarose gel that demonstrates the quality (integrity) of the released and isolate nucleic acid of FIG. 7.

When the released nucleic acid was analyzed by gel electrophoresis, high molecular weight nucleic acid was apparent in all reaction compositions containing HDTAB (see FIG. 8). High molecular weight nucleic acid was also present in reaction compositions containing CTACl and either 1-methy-2-pyrolidinone or acridine orange.

High molecular weight nucleic acid was also observed in the reaction composition comprising HDTACl and 1-methyl-2-pyrolidinone.

EXAMPLE 9

Example 7 demonstrated that the presence of certain reagents that have been used to stabilize RNA in tissue samples (i.e. Streck Tissue Fixative and RNA Later) inhibited the activity of Proteinase K. To attempt to reduce this inhibition, tissue was pre-incubated in several reagents to allow them to diffuse into the sample. Residual reagent was removed prior to incubation of the samples in reaction compositions.

Liver slices were incubated in various solutions prior to exposure to reaction compositions as follows. Slices of liver tissue (94–330 mg/sample) were placed into four sets of six Eppendorf tubes. Five hundred microliters of either Nucleic Acid Purification Lysis Solution, RNA Later, or Streck Tissue Fixative was added to one set of tubes. The fourth set of tubes contained no pretreatment solution and served as a control.

The tubes were incubated for 4 hours at 4° C., then centrifuged in an Eppendorf microfuge (Model 5415C) at ambient temperature for 2 minutes at 14,000 RPM. The supernatant was discarded and four hundred microliters of a reaction composition comprising 100 mM MES, pH 6.0, 20 mM $CaCl_2$, and 1 mg Proteinase K, was added to each tube. One of the six additional components shown in Table 9 was also added to each tube. The tubes were incubated at 45° C. with mixing (Eppendorf Thermomixer, Model 5436) for 30 minutes.

The resulting surfactant:protease complex was solubilized using methods the same as or similar to those described in Example 7. Remaining tissue fragments were removed by centrifugation using methods the same as or similar to those described in Example 7. The supernatant was phenol extracted, isopropanol precipitated, and ethanol washed using methods the same as or similar to those described in Example 6. The washed nucleic acid pellets were resuspended and the amount of nucleic acid released and the integrity of that nucleic acid were evaluated using methods the same as or similar to those described in Example 6.

TABLE 9

| Tube | Additional Reaction Composition Components |
| --- | --- |
| 1 | 1% Cetyltrimethylammonium Bromide (CTAB) |
| 2 | 1% CTAB, 10% 1-methyl-2-pyrolidinone (NMP) |
| 3 | 1% CTAB, 200 µg/mL Acridine Orange |
| 4 | 1% Cetyltrimethylammonium Chloride (CTACl) |
| 5 | 1% CTACl, 10% NMP |
| 6 | 1% CTACl, 200 µg/mL Acridine Orange |

Figure 9:
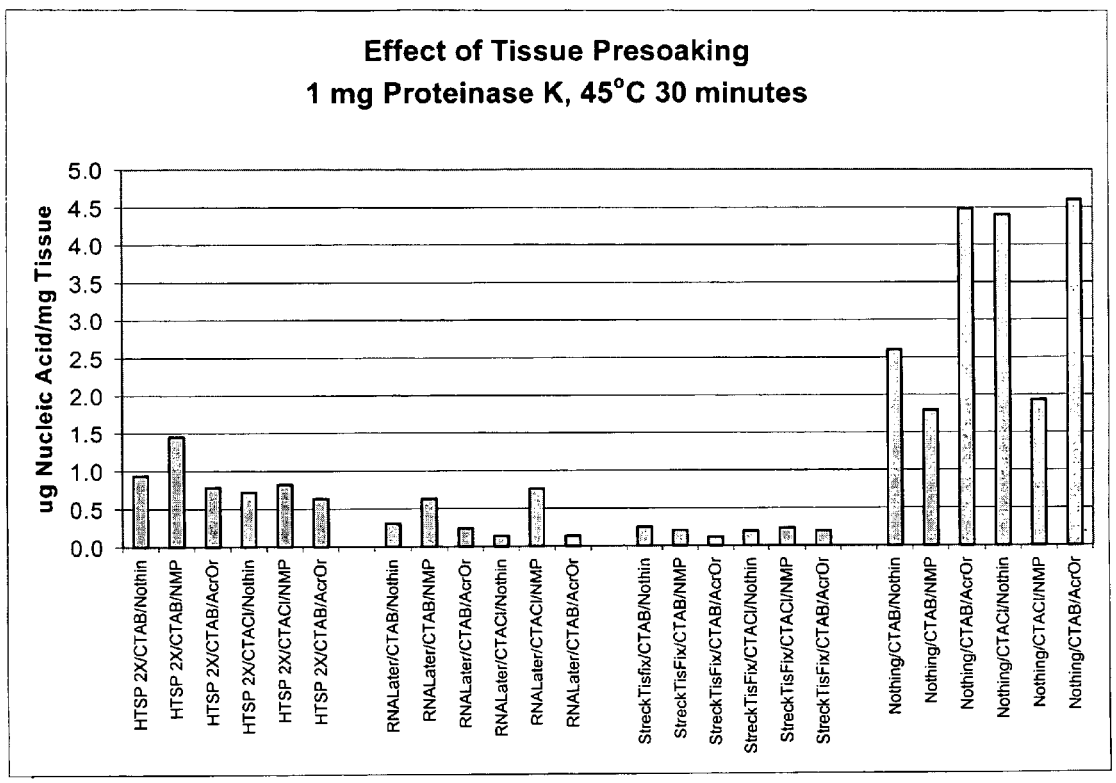
FIG. 9: illustrates the effect of exposing liver slices to pretreatment solutions prior to incubation for 30 minutes at 45° C. in reaction compositions comprising 1 mg/mL Proteinase K and the indicated surfactants and additives. When used in these figures, HTSP 2X means Nucleic Acid Purification Lysis Solution; AcrOr means acridine orange.
Figure 10:
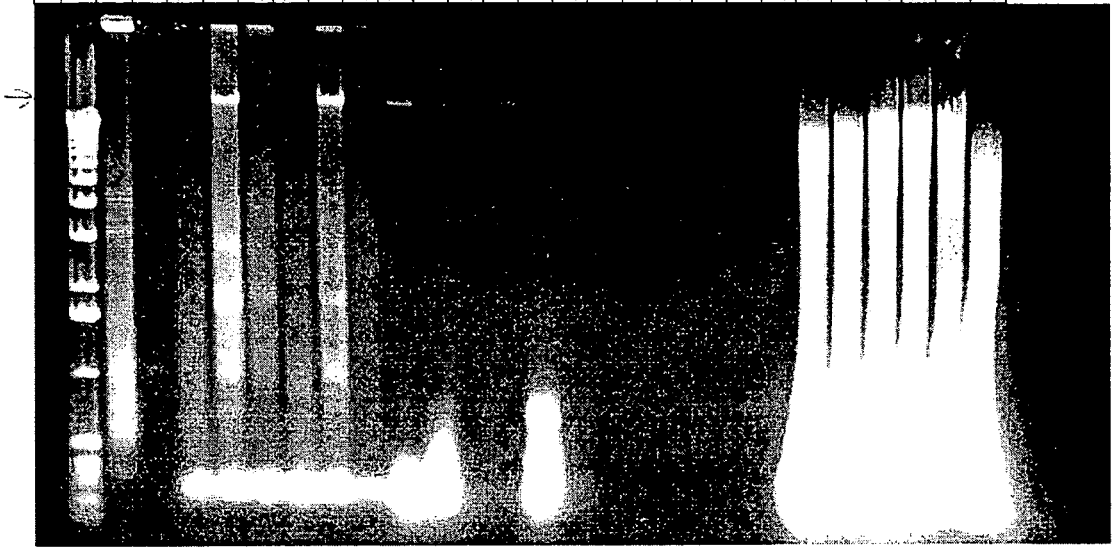
FIG. 10: depicts a stained agarose gel that demonstrates the quality of nucleic acid released and isolated from samples that were incubated in pretreatment solutions prior to surfactant:Proteinase K treatment.

As shown in FIG. 9, pretreatment of the samples with one of the pretreatment solutions resulted in a decreased amount of $A_{260}$-absorbing material that was released when compared to the control.

EXAMPLE 10

The ability of aurintricarboxylic acid to maintain the integrity of the nucleic acid released using reaction compositions comprising CTAB, CTACl, or SDS, was evaluated. Aurintricarboxylic acid is believed to inhibit the binding of proteins, e.g., nucleases, to nucleic acid and has been demonstrated to inhibit ribonucleases. Slices of liver tissue (77–186 mg/sample) were placed into twenty-one Eppendorf tubes. To each tube was added 400 µL of a reaction composition comprising 50 mM MES, pH 6.0, 20 mM $CaCl_2$, and additional components as shown in Table 10.

Table 10. Additional Reaction Composition Components

TABLE 10

| | Additional Reaction Composition Components |
| --- | --- |
| Tube | Additional Reaction Composition Components |
| 1 | 1% CTAB, 5 mM Aurintricarboxylic Acid |
| 2 | 1% CTAB, 2 mM Aurintricarboxylic Acid |
| 3 | 1% CTAB, 1 mM Aurintricarboxylic Acid |
| 4 | 1% CTAB, 0.5 mM Aurintricarboxylic Acid |
| 5 | 1% CTAB, 0.2 mM Aurintricarboxylic Acid |
| 6 | 1% CTAB, 0.1 mM Aurintricarboxylic Acid |

TABLE 10-continued

| | Additional Reaction Composition Components |
| --- | --- |
| Tube | Additional Reaction Composition Components |
| 7 | 1% CTAB |
| 8 | 1% CTACl, 5 mM Aurintricarboxylic Acid |
| 9 | 1% CTACl, 2 mM Aurintricarboxylic Acid |
| 10 | 1% CTACl, 1 mM Aurintricarboxylic Acid |
| 11 | 1% CTACl, 0.5 mM Aurintricarboxylic Acid |
| 12 | 1% CTACl, 0.2 mM Aurintricarboxylic Acid |
| 13 | 1% CTACl, 0.1 mM Aurintricarboxylic Acid |
| 14 | 1% CTACl |
| 15 | 1% SDS, 5 mM Aurintricarboxylic Acid |
| 16 | 1% SDS, 2 mM Aurintricarboxylic Acid |
| 17 | 1% SDS, 1 mM Aurintricarboxylic Acid |
| 18 | 1% SDS, 0.5 mM Aurintricarboxylic Acid |
| 19 | 1% SDS, 0.2 mM Aurintricarboxylic Acid |
| 20 | 1% SDS, 0.1 mM Aurintricarboxylic Acid |
| 21 | 1% SDS |

The tubes were incubated at 55° C. with mixing (Eppendorf Thermomixer, Model 5436) for 30 minutes. The resulting surfactant-protease complex was solubilized using methods the same as or similar to those described in Example 7. Undigested tissue fragments were removed by centrifugation using methods the same as or similar to those described in Example 7. The supernatant was phenol extracted, isopropanol precipitated and ethanol washed using methods the same as or similar to those described in Example 6. The washed nucleic acid pellets were resuspended and the integrity of the released nucleic acid were evaluated using methods the same as or similar to those described in Example 6.

Figure 11:
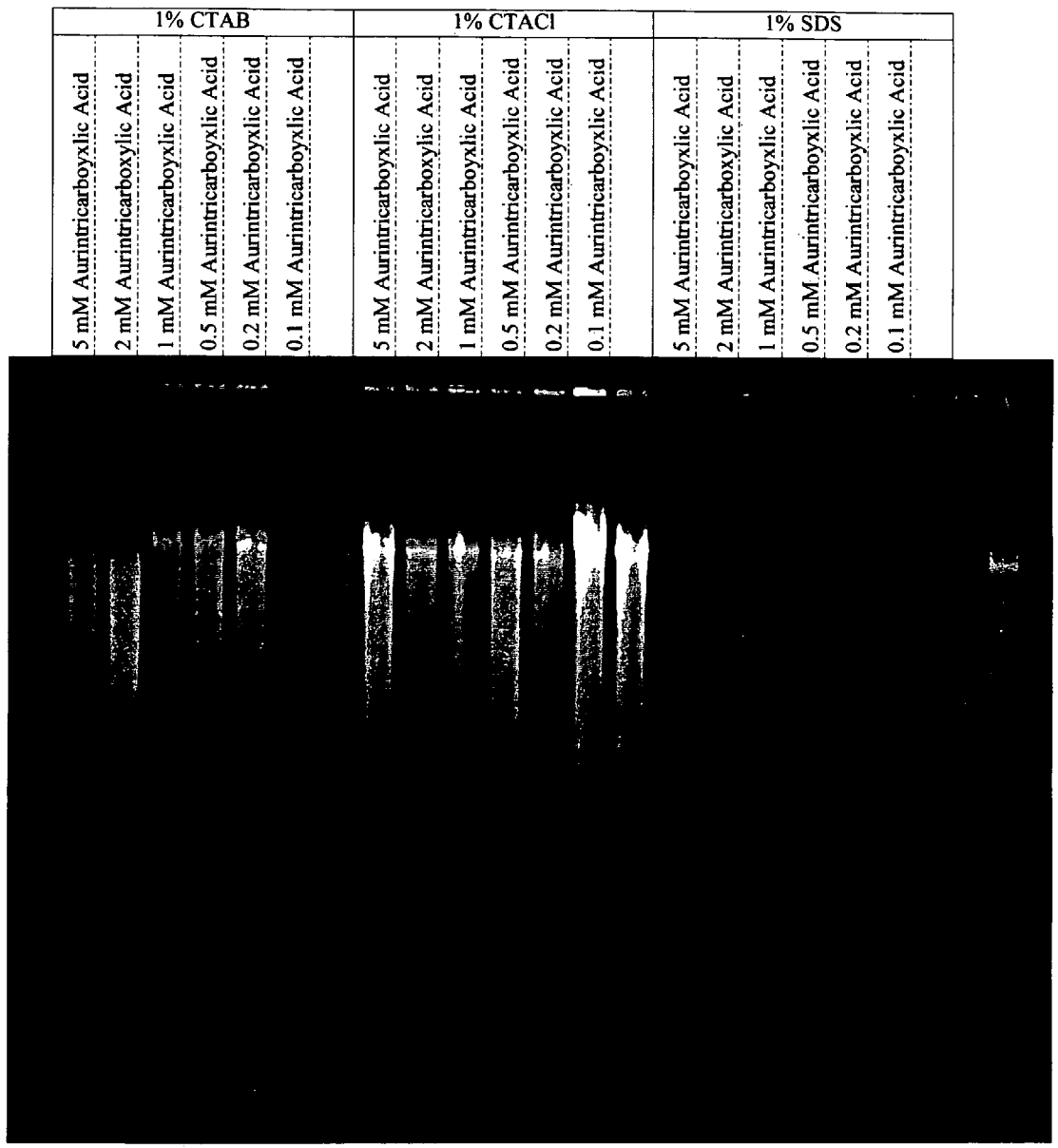
FIG. 11: depicts a stained agarose gel that demonstrates the quality of nucleic acid released and isolated using reaction compositions comprising varying amounts of aurintricarboxylic acid.

As shown in FIG. 11, the presence of aurintricarboxylic acid in the reaction composition enhanced the yield of high molecular weight nucleic acid. Reaction compositions containing aurintricarboxylic acid and either CTAB or CTACl released a large amount of high integrity nucleic acid. When SDS was the surfactant in the reaction composition, less nucleic acid was released.

EXAMPLE 11

To examine the ability of other cationic reagents to release high integrity nucleic acid, additional compounds were tested as follows. Slices of liver tissue (80–140 mg/sample) were placed into fourteen Eppendorf tubes. Five hundred microliters of a reaction composition comprising 100 mM MES, pH 6, 20 mM $CaCl_2$, 0.5 mM aurintricarboxylic acid (e.g., Sigma #A1895), and 1 mg Proteinase K, was added to each tube. One of the cationic reagents shown in Table 11, was added to each tube to a final concentration of 1%. As a control, one tube contained no additional reagent. The tubes were incubated at 60° C. for 30 minutes with mixing (Eppendorf Thermomixer, Model 5436). Following the incubation, 200 µL of a solution containing 1.75 M NaCl, 29% Tween 20, and 585 µg/mL glycogen (resulting in a final concentration of 447 mM NaCl, 7.5% Tween 20, and 149 µg/mL glycogen) was added to each tube to dissolve the surfactant:nucleic acid complex. The remaining tissue fragments were removed by centrifugation using methods the same as or similar to those described in Example 7. The supernatant was phenol extracted, isopropanol precipitated, and ethanol washed using methods the same as or similar to those described in Example 6. The washed nucleic acid pellets were resuspended in 100 µL 10 mM Tris, pH 8.0, 0.1 mM EDTA, and 1 unit/µL Rnasin. The amount of nucleic acid released and its integrity were evaluated using methods the same as or similar to those described in Example 6.

TABLE 11

| Tube | Cationic Reagent |
|---|---|
| 1 | dodecyltrimethylammonium bromide (DTAB) |
| 2 | tetradecyltrimethylammonium bromide (TTAB) |
| 3 | CTAB |
| 4 | CTACl |
| 5, 6 | HTAB |
| 7 | Mackernium 006 (polyquaternium 6) |
| 8 | Mackernium (Olealkonium chloride) |
| 9 | Mackernium NLE (Quaternium-84) |
| 10 | Mackernium 007 (Polyquaternium 7) |
| 11 | Mackernium Stearalkonium SDC85 Chloride |
| 12 | Benzalkonium chloride |
| 13 | SDS |

Figure 12:
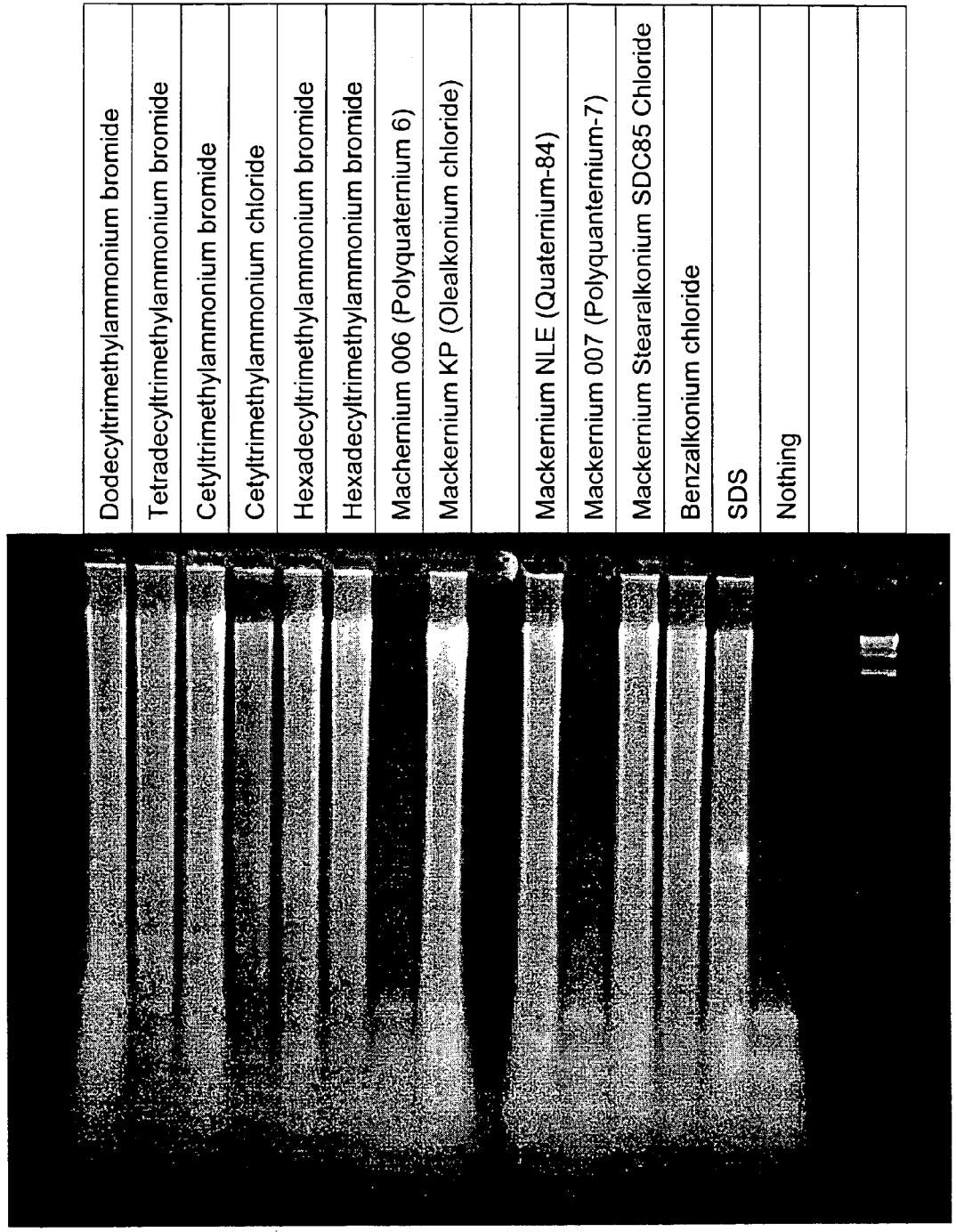
FIG. 12: depicts a stained agarose gel that provides a comparison of the amount and integrity of nucleic acid released and isolated with various cationic compounds.

As shown in FIG. 12, all of the cationic reagents tested, except for Mackernium 006 and 007, released high integrity nucleic acid. Of the eleven cationic reagents tested, nine were surfactants and two, Mackernium 006 and 007, were cationic polymers. This result demonstrates that, under these conditions, all of the cationic surfactants when used in conjunction with Proteinase K, effectively released nucleic acid from the sample.

While the present invention has been described in terms of these exemplary embodiments, the skilled artisan will readily understand that numerous variations and modifications of these exemplary embodiments are possible without undue experimentation. All such variations and modifications are within the intended scope of the claimed invention.

What is claimed is:

1. A composition for macerating whole tissue, wherein the whole tissue is not a microorganism, a virus, or blood, comprising: at least one cationic surfactant, at least one protease, a buffer, and a salt at a concentration of about 550 mM or less, wherein the cationic surfactant accelerates maceration of the whole tissue by the at least one protease.

2. The composition of claim 1, wherein the at least one cationic surfactant is protonated under the conditions used.

3. The composition of claim 1, wherein the at least one cationic surfactant has the structure:

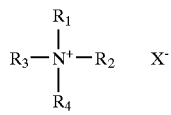

wherein $R_1$, $R_2$, $R_3$, and $R_4$ are independently selected from the group consisting of: —H; an alkyl group comprising between one and twenty carbon atoms; and an aryl group comprising between six to twenty-six carbon atoms.

4. The composition of claim 3, wherein the cationic surfactant is an alkyltrimethyl ammonium salt, where $R_1$, $R_2$, and $R_3$ are methyl groups, and $R_4$ is an alkyl group comprising 6, 8, 10, 12, 14, 16, or 18 carbon atoms.

5. The composition of claim 4, where the cation of the alkyltrimethyl ammonium salt is selected from the group consisting of cetyltrimethylammonium, hexadecyltrimethylammonium, tetradecyltrimethylammonium, dodecyltrimethylammonium, and lauryl trimethylammonium.

6. The composition of claim 4, where the anion ($X^-$) of the alkyltrimethyl ammonium salt is bromide, chloride, iodide, hydroxide, nitrate, sulfate, phosphate, formate, acetate, propionate, oxalate, malonate, succinate, or citrate.

7. The composition of claim 3, wherein the at least one cationic surfactant is a benzyldimethyl-n-alkylammonium salt, where $R_1$ and $R_2$ are methyl groups, $R_3$ is an aryl group comprising six carbon atoms, and $R_4$ is an alkyl group comprising 6, 8, 10, 12, 14, 16, or 18 carbon atoms.

8. The composition of claim 7, where the anion of the benzyldimethyl-n-alkylammonium salt is selected from the group consisting of bromide, chloride, iodide, hydroxide, nitrate, sulfate, phosphate, formate, acetate, propionate, oxalate, malonate, succinate, and citrate.

9. The composition of claim 1, wherein the at least one protease is selected from the group consisting of subtilisins, subtilases, and alkaline serine proteases.

10. The composition of claim 1, wherein the at least one protease is selected from the group consisting of Proteinase K, Proteinase R, Proteinase T, Subtilisin DY, an alkaline serine protease from *Streptomyces griseus* or *Bacillus licheniformis*, Dispase, subtilisin Carlsberg, subtilopeptidase A, and thermolysin.

11. The composition of claim 9, wherein the protease is Proteinase K.

12. The composition of claim 9, wherein the protease is thermolysin or a thermostable protease.

13. The composition of claim 12, wherein the protease is from Thermus Rt41A or *Bacillus thermoproteolyticus rokko*.

14. The composition of claim 1, further comprising calcium chloride.

15. The composition of claim 1, wherein the buffer maintains the pH between pH 7 and pH 9.

16. The composition of claim 1, wherein the buffer maintains the pH between pH 5 and pH 7.

17. The composition of claim 1, further comprising at least one ribonuclease inhibitor.

18. The composition of claim 17, wherein the at least one ribonuclease inhibitor comprises aurintricarboxylic acid, vanadylate ribonucleoside complexes, phenylglyoxal, p-hydroxyphenylglyoxal, polyamines, spermidine, 9-aminoacridine, iodoacetate, bentonite, poly[2'-O-(2,4-dinitrophenyl)] poly(adenyhlic acid), zinc sulfate, bromopyruvic acid, formamide, copper, or zinc.

19. The composition of claim 18, wherein the at least one ribonuclease inhibitor comprises aurintricarboxylic acid.

20. The composition of claim 1, wherein the cationic surfactant is cetyltrimethylammonium bromide (CTAB), cetyltrimethylammonium chloride (CTACI), hexadecyltrimethylammonium bromide, or hexadecyltrimethylammonium chloride; the protease is Proteinase K; the buffer maintains the pH between pH 5 and pH 7; and further comprising aurintricarboxylic acid.

21. The composition of claim 20, further comprising at least one solubilizing agent for enhancing the solubility or permeability of the sample.

22. The composition of claim 21, wherein the solubilizing agent is 1-methyl 2 pyrolidinone, N-methylpyrolidinone, pyrolidinone, dimethylformamide, or dimethylsulfoxide.

23. The composition of claim 1, further comprising at least one deoxyribonuclease inhibitor.

24. The composition of claim 23, wherein the at least one deoxyribonuclease inhibitor comprises a divalent cation chelator.

25. The composition of claim 24, wherein the chelator is EDTA, EGTA, of DPTA.

26. A composition for macerating whole tissue, wherein the whole tissue is not a microorganism, a virus, or blood, comprising: at least one cationic surfactant, at least one protease, a buffer, and the whole tissue, wherein the at least one cationic surfactant is selected from:

a) an alkyltrimethyl ammonium salt having the structure:

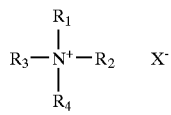

wherein $R_1$, $R_2$, and $R_3$ are methyl groups, and $R_4$ is an alkyl group, comprising 6, 8, 10, 12, 14, 16, or 18 carbon atoms; and b) a benzyldimethyl-n-alkylammonium salt having the structure:

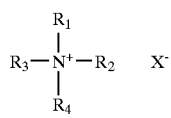

wherein $R_1$ and $R_2$ are methyl groups. $R_3$ is an aryl group comprising six carbon atoms, and $R_4$ is an alkyl group comprising 6, 8, 10, 12, 14, 16, or 18 carbon atoms.

27. The composition of claim 26, wherein the at least one cationic surfactant is protonated under the conditions used.

28. The composition of claim 26, wherein the at least one cationic surfactant is the alkyltrimethyl ammonium salt of a), and where the cation of the alkyltrimethyl ammonium salt is selected from the group consisting of cetyltrimethylammonium, hexadecyltrimethylammonium, tetradecyltrimethylammonium, dodecyltrimethylammonium, and lauryl trimethylammonium.

29. The composition of claim 26, wherein the at least one cationic surfactant is the alkyltrimethyl ammonium salt of a), and where the anion ($X^-$) of the alkyltrimethyl ammonium salt is bromide, chloride, iodide, hydroxide, nitrate, sulfate, phosphate, formate, acetate, propionate, oxalate, malonate, succinate, or citrate.

30. The composition of claim 26, wherein the at least one cationic surfactant is the benzyldimethyl-n-alkylammonium salt of b), and where the anion of the benzyldimethyl-n-alkylammonium salt is selected from the group consisting of bromide, chloride, iodide, hydroxide, nitrate, sulfate, phosphate, formate, acetate, propionate, oxalate, malonate, succinate, and citrate.

31. The composition of claim 26, wherein the at least one protease is selected from the group consisting of subtilisins, subtilases, and alkaline serine proteases.

32. The composition of claim 31, wherein the at least one protease is selected from the group consisting of Proteinase K, Proteinase R, Proteinase T, Subtilisin DY, an alkaline serine protease from *Streptomyces griseus* or *Bacillus licheniformis*, Dispase, subtilisin Carlsberg, subtilopeptidase A, and thermolysin.

33. The composition of claim 31, wherein the protease is Proteinase K.

34. The composition of claim 31, wherein the protease is thermolysin or a thermostable protease.

35. The composition of claim 34, wherein the protease is from Thermus Rt41A or *Bacillus thermoproteolyticus rokko*.

36. The composition of claim 26, further comprising calcium chloride.

37. The composition of claim 26, wherein the buffer maintains the pH between pH 7 and pH 9.

38. The composition of claim 26, wherein the buffer maintains the pH between pH 5 and pH 7.

39. The composition of claim 26, further comprising at least one ribonuclease inhibitor.

40. The composition of claim 39, wherein the at least one ribonuclease inhibitor comprises aurintricarboxylic acid, vanadylate ribonucleoside complexes, phenylglyoxal, p-hydroxyphenylglyoxal, polyamines, spermidine, 9-aminoacridine, iodoacetate, bentonite, poly[2'-O-(2,4-dinitrophenyl)] poly(adenyhlic acid), zinc sulfate, bromopyruvic acid, formamide, copper, or zinc.

41. The composition of claim 39, wherein the at least one ribonuclease inhibitor comprises aurintricarboxylic acid.

42. The composition of claim 26, wherein the cationic surfactant is cetyltrimethylammonium bromide (CTAB), cetyltrimethylammonium chloride (CTACl), hexadecyltrimethylammonium bromide, or hexadecyltrimethylammonium chloride; the protease is Proteinase K; the buffer maintains the pH between pH 5 and pH 7; and further comprising aurintricarboxylic acid.

43. The composition of claim 42, further comprising at least one solubilizing agent for enhancing the solubility or permeability of the sample.

44. The composition of claim 43, wherein the solubilizing agent is 1-methyl 2 pyrolidinone, N-methylpyrolidinone, pyrolidinone, dimethylformamide, or dimethylsulfoxide.

45. The composition of claim 26, further comprising at least one deoxyribonuclease inhibitor.

46. The composition of claim 45, wherein the at least one deoxyribonuclease inhibitor comprises a divalent cation chelator.

47. The composition of claim 46, wherein the chelator is EDTA, EGTA, of DPTA.

* * * * *